(12) United States Patent
Entenberg et al.

(10) Patent No.: US 11,712,205 B2
(45) Date of Patent: Aug. 1, 2023

(54) HIGH RESOLUTION INTRAVITAL IMAGING AND USES THEREOF

(71) Applicant: Albert Einstein College of Medicine, Bronx, NY (US)

(72) Inventors: David Entenberg, Granite Springs, NY (US); John S. Condeelis, Bronx, NY (US); Sonia E. Voiculescu, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 125 days.

(21) Appl. No.: 16/640,869

(22) PCT Filed: Aug. 1, 2018

(86) PCT No.: PCT/US2018/044737
§ 371 (c)(1),
(2) Date: Feb. 21, 2020

(87) PCT Pub. No.: WO2019/040244
PCT Pub. Date: Feb. 28, 2019

(65) Prior Publication Data
US 2020/0352516 A1    Nov. 12, 2020

Related U.S. Application Data

(60) Provisional application No. 62/548,455, filed on Aug. 22, 2017.

(51) Int. Cl.
*A61B 5/00* (2006.01)
*A61B 5/08* (2006.01)
*G02B 21/36* (2006.01)

(52) U.S. Cl.
CPC ............ *A61B 5/704* (2013.01); *A61B 5/0068* (2013.01); *A61B 5/0071* (2013.01); *A61B 5/08* (2013.01); *A61B 5/418* (2013.01); *A61B 5/4222* (2013.01); *A61B 5/4872* (2013.01); *G02B 21/367* (2013.01); *A61B 2503/42* (2013.01)

(58) Field of Classification Search
CPC ............................ A61B 5/704; A61B 5/0068
See application file for complete search history.

(56) References Cited

U.S. PATENT DOCUMENTS

| 2005/0123181 | A1 | 6/2005 | Freund et al. |
| 2007/0206275 | A1 | 9/2007 | Hemmer et al. |
| 2009/0185980 | A1 | 7/2009 | Dong et al. |
| 2010/0265574 | A1 | 10/2010 | Kasahara |
| 2012/0170828 | A1 | 7/2012 | Gareau et al. |

FOREIGN PATENT DOCUMENTS

WO    2017/059397 A1    4/2017

*Primary Examiner* — Joseph M Santos Rodriguez
(74) *Attorney, Agent, or Firm* — Fox Rothschild LLP

(57) ABSTRACT

Methods and apparatus are provided for high resolution intravital imaging and for chronic optical imaging of tissues such as lung.

29 Claims, 23 Drawing Sheets

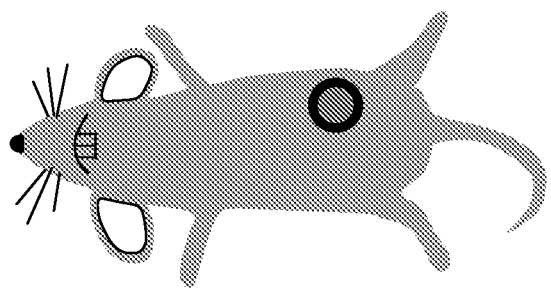
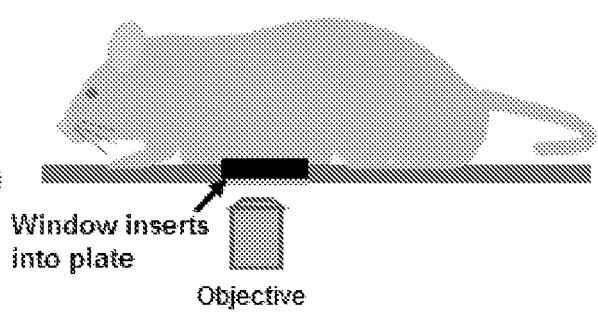
FIG. 1A					FIG. 1B
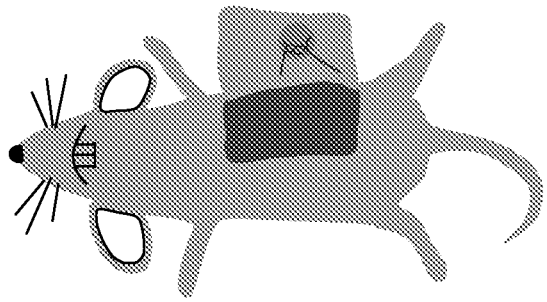
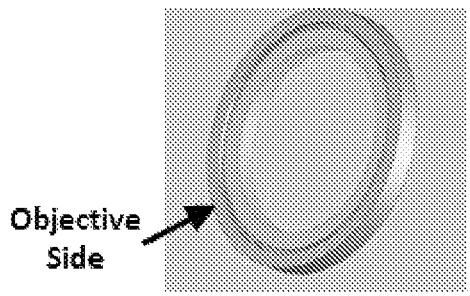
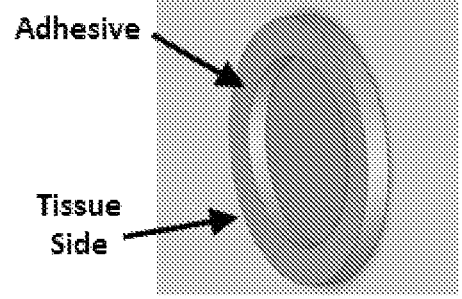
FIG. 1C
FIG. 1E
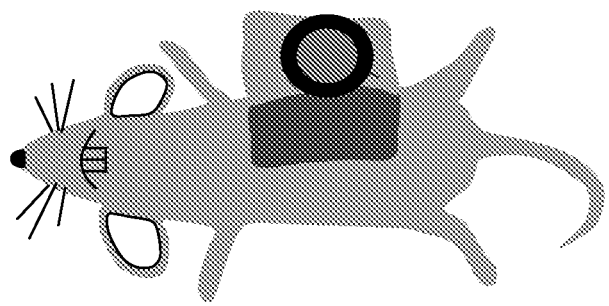
FIG. 1D

HIGH RESOLUTION INTRAVITAL IMAGING AND USES THEREOF

CROSS REFERENCE TO RELATED APPLICATIONS

This application claims the benefit of U.S. Provisional Patent Application No. 62/548,455, filed on Aug. 22, 2017, the contents of which are hereby incorporated by reference.

This invention was made with government support under grant numbers CA100324, CA200561 and CA216248 awarded by the National Institutes of Health. The government has certain rights in the invention.

BACKGROUND OF THE INVENTION

Throughout this application various publications are referred to in parentheses. Full citations for these references may be found at the end of the specification. The disclosures of all publications, patents and patent applications mentioned herein are hereby incorporated by reference in their entirety into the subject application to more fully describe the art to which the subject invention pertains.

Imaging in both medicine and research has proven to be crucial to understanding the structure and function of many tissues in health and disease. Clinical imaging modalities (PET, MRI, CT, etc.) allow a view of whole organs non-invasively. However, the low spatial resolution of these modalities prevents visualization of the earliest stages of disease onset, and determination of cause and effect relationships during tumor progression. Understanding these earliest stages and cause and effect relationships provides new opportunities for therapeutic intervention.

Optical imaging modalities (e.g. confocal, multiphoton) have the ability to detect and image tissues with single-cell resolution. However, imaging of internal organs, particularly those of the thoracic cavity, presents several challenges arising from both their inaccessibility and their constant motion. One organ of particular interest is the lung, the site of many pathologies including acute sickle cell crisis, lung cancer, asthma, and metastatic disease.

Pathologists rely on microscopy to diagnose disease states in tissues and organs. They utilize both high-resolution, high-magnification images to interpret the staining and morphology of individual cells, as well as low-magnification overviews to give context and location to these cells. Low magnification images inform about the tissue wide structure and architecture, and are used to identify regions of the tissue for further analysis at high magnification. The high magnification analysis then reveals the identity of individual cells (based upon their staining and cellular and nuclear morphology), and the spatial relationships between them. While this switch between low and high magnification occurs repeatedly throughout histopathologic analysis, the low magnification perspective is most often not obtained in live tissue imaging, leading to a loss of tissue wide context. Intravital imaging is a powerful technique for studying cells and tissues in their native, live environment and can yield sub-cellular resolution images similar to those used by pathologists. However, technical limitations prevent the straightforward acquisition of low-magnification images during intravital imaging, and they are hence not typically captured. The major reason for this underutilization of low magnification views arises from multiphoton microscopy's reliance upon high-magnification, high-numerical-aperture objective lenses for efficient and bright signal generation. Low magnification lenses typically do not generate enough multiphoton signal to create high quality images. The serial acquisition, mosaicking, and stitching together of many high-resolution, high-magnification fields of view is a technique that overcomes these limitations in fixed and ex vivo tissues. The technique however, has not to date been widely applied to intravital imaging as movements caused by the living animal induce image distortions that are difficult to compensate for computationally.

Recent technological advancements have enabled sub-cellular resolution optical imaging of the murine lung over periods of up to 12 hrs (Entenberg et al. 2015, Looney et al. 2011). These techniques have provided the first high-resolution images of the living, breathing lung. They accomplish this by mechanically ventilating the animal, resecting the ribcage, and immobilizing the lung tissue using a vacuum. As such, they are extremely invasive, terminal surgeries which are limited in duration and do not allow more than one imaging session. This prevents their application to processes such as spontaneous metastatic progression that take longer than 12 hrs to manifest. In addition, there may be artifacts associated with vacuum immobilization of the lung such as compression of blood vessels, which affects vascular flow. Having the ability to perform high-resolution optical imaging in metastatic sites such as the lung (the most common site of metastasis in breast cancer), over days to weeks, would enable the study and identification of commonalities between metastases and the primary tumors from which they derive, identification of the mechanism by which pre-metastatic niche formation affects tumor cell fate in the lung, and the observation of differences between experimental and spontaneous lung metastasis seeding and progression.

The present invention provides techniques for the stabilization of numerous tissues, including extremely compliant tissues, that have traditionally been extremely difficult to image and provides a Window for High Resolution Imaging of the Lung (WHRIL), which allows repeated optical imaging over a period of days to weeks.

SUMMARY OF THE INVENTION

The present invention provides methods and apparatus for high resolution intravital imaging and for chronic long term optical imaging of internal organs including the lung. The invention provides methods and apparatus for the stabilization and imaging of large volumes of tissue in all visceral organs including lung at 0.25 µm resolution. The invention allows the novel benefit of being able to return to the tissue day after day over weeks with the use of permanent windows in the mechanical stabilization step.

BRIEF DESCRIPTION OF THE DRAWINGS

FIG. 1A-1E. Overview of surgical protocol. A) With implantable imaging windows such as the mammary, abdominal, or even lung imaging windows, the window itself provides a stable frame that keeps the tissue hydrated and immobilized relative to the glass. However, involuntary movements such as heart beat and respiration still cause movement of the tissue and window together. B) Inserting the window frame into a tight-fitting fixturing stage plate that is fixed relative to the objective lens completely immobilizes both the window frame and tissue. C) With skin flap surgeries, the tissue of interest (e.g. tumor, mammary fat pad, lymph node, salivary gland, etc.) is exposed by surgical incision through the skin. D) The conditions for stable imaging that are possible when using imaging windows can be recreated by attaching a cover-glass inset into a shallow window frame over the tissue of interest. Adhesive placed under the window frame, away from the tissue under study, immobilizes the tissue relative to the frame. The window frame can then be inserted as in B) into a tight-fitting fixturing stage plate. E) 3D computer aided designs of the shallow window frame and cover-glass described in D).

DETAILED DESCRIPTION OF THE INVENTION

Figure 2A:
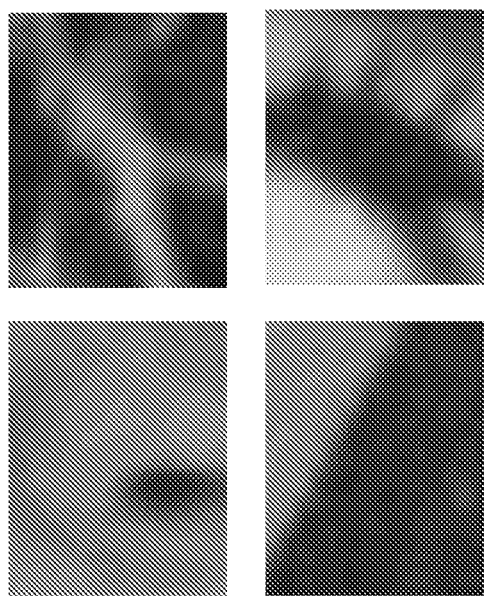
FIG. 2A-2D. Multi-scale imaging provides detail and context by acquiring many high-magnification images sequentially and stitching them together to form a low magnification overview image. A) The acquisition of just a few individual fields of view does not provide enough context to understand fully the imaged subject. B) Information about the subject is improved by increasing the number of acquisitions, however, without maintaining the spatial relationship between the individual images, the overall context remains obscured. C) Acquisition and arrangement of the images in a specific order (numbers) maintains the spatial relationship of the images. D) Final stitching of the image reveals the overall context while preserving the original resolution of the underlying images.

The present invention provides a method of high-resolution intravital imaging of a tissue of interest in a subject using a microscope comprising:

a) exposing the tissue of interest in the subject, b) attaching a window frame holding a transparent window to the subject so that the tissue of interest is viewable through the window, c) attaching the window frame to a microscope stage with a window fixturing plate that is movable relative to the optical axis of the microscope in at least x- and y-directions, and d) acquiring through the window high-magnification, high-resolution overlapping images of the tissue of interest in a mosaic pattern and stitching the images together to produce a low-magnification, high-resolution overview image of the tissue of interest that preserves subcellular resolution, thereby obtaining high-resolution intravital images of a tissue of interest in a subject.

As used herein, "high magnification" refers to an image taken with resolution at the theoretical optical diffraction limit. These images typically have a field of view of ~85×85 µm or 7225 µm². "Low magnification" refers to an image taken so as to cover a field of view spanning several millimeters. These images typically have a field of view up to ~5 mm×5 mm or 25 mm². The range of magnification for this invention thus spans a 3460 fold difference.

"Stitching" is the process of combining multiple spatially related images, potentially with overlapping fields of view, to produce a large image with a number of pixels that is approximately the sum of the number of pixels composing each of the individual images.

In one embodiment, the fixturing plate comprises portions defining a circular hole for the window and a circular recess that holds the window frame. In one embodiment, the fixturing plate comprises portions defining a slotted recess that holds the window frame. The fixturing plate can be made, for example, of metal and/or plastic. The size of the fixturing plate can vary depending on the tissue and species of subject being imaged. Representative sizes for mice are 4-5 mm for imaging the lung and 15 mm for imaging other tissues.

The window frame can be attached to the subject using adhesive, such as, for example, cyanoacrylate. In one embodiment, the window frame is attached to the tissue of interest and saline is applied within the window frame before the window is affixed to the window frame to cover the tissue of interest with saline.

Additional stabilization of the tissue of interest can be provided by affixing a rigid backing to a side of the tissue of interest opposite to the objective lens of the microscope. The rigid backing can be made, for example, of one or more of rubber, plastic and metal. The tissue for which additional stabilization may be desirable is, for example, a mammary fat-pad, lymph node or salivary gland.

In one embodiment, the window frame is made of stainless steel and passivation of the window frame is carried out before the window frame is attached to the subject.

In one embodiment, the fixturing plate can be placed between the skin of the subject and the outside lip of the window frame to stabilize the window and the tissue of interest, and the fixturing plate is secured to the microscope stage. In one embodiment, the fixturing plate has a recess for holding the window frame, and the close tolerance of the recess stabilizes the window frame and tissue of interest.

The window frame can comprise a plurality of fiducial markers. The fiducial markers can serve as navigational reference points and, along with the xy stage origination, can form a set of vectors from which a coordinate transformation connecting repeated imaging sessions can be derived.

The window frame can comprise a beveled edge that rests against the tissue of interest, a groove into which a skin flap or ribcage fits, and a recess for the window.

Images can be obtained using a low-magnification, high-numerical aperture, long-working distance objective lens, such as, for example, a 25× 1.05 NA lens.

The tissue can be imaged, for example, to a depth of at least 100 µm with a step size of 5 µm between each z-slice.

Preferably, the images are obtained in a specific order so that the spatial relationships of the images are maintained and the overall architecture of the tissue is reconstructed.

Cells or other structures in the tissue of interest can be labeled using genetically encoded fluorescent proteins or injectable fluorescent dyes.

The tissue of interest can be any tissue, and is preferably liver, lung, kidney, pancreas, colon, intestines, stomach, esophagus, ovary, uterus, bladder, prostate, bone marrow, brain, mammary gland, lymph node or salivary gland tissue. The window frame and window can be chronically implanted in the subject over the tissue of interest.

The invention also provides a method for chronic intravital imaging of the lung of a subject using a microscope, comprising:

making a circular incision through the skin and adjacent ribs of an anesthetized subject lateral to the sternum and superior to the last floating rib, securing a window frame in the incision so that the adjacent ribs are positioned in a groove of the window frame, wherein the window frame comprises fiducial marks, adhering the window frame to lung tissue by raising the window frame away from the lung tissue, dispensing a quick-setting adhesive on the underside of the window frame, and expanding the lung to make contact with the window frame until the adhesive sets, suturing tissue around the window frame to provide a complete surgical closure, sealing the thoracic cavity by applying an adhesive to a window and adhering it to the expanded lung tissue and the inner recess of the window frame, and following recovery of the subject from anesthesia, stabilizing motion of the window frame for imaging by placing a fixturing plate, comprising portions defining a slotted recess sized to accommodate the window frame, between skin of the subject and an outside lip of the window frame, and placing the subject on the stage of the microscope.

Figure 18:
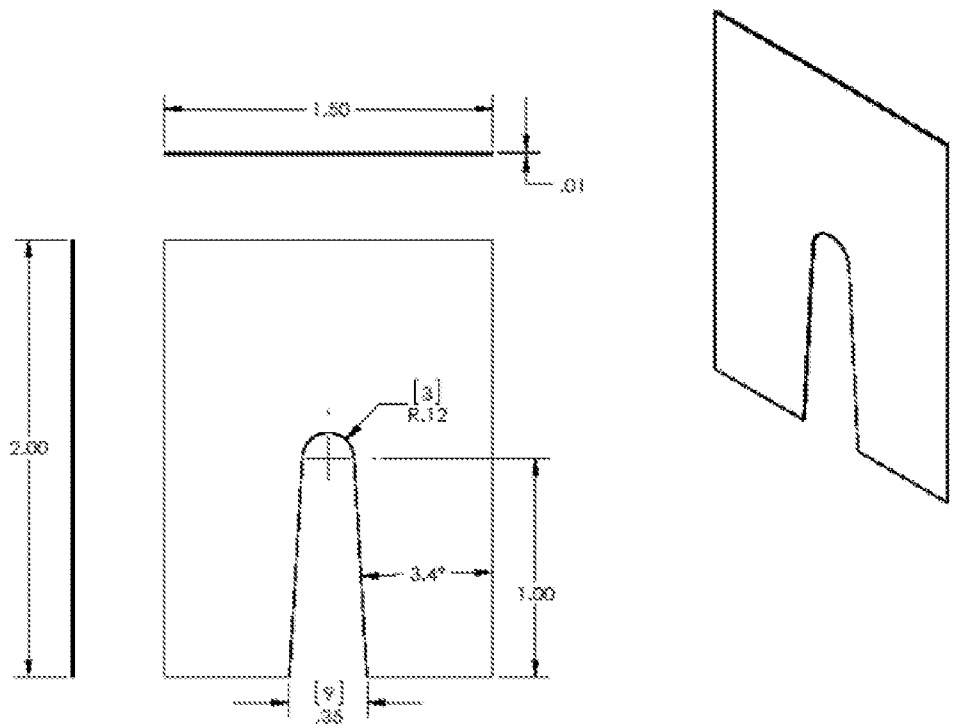
FIG. 18. Further example of the fixturing plate shown in FIG. 12D.
Figure 19A:
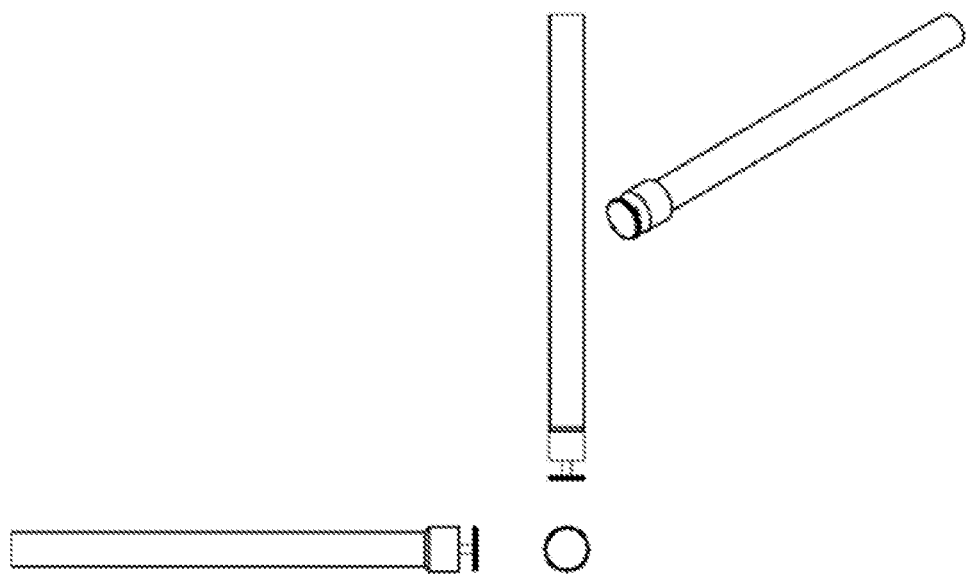
FIG. 19A-19B. Examples of a rib cutting tool. A) The tool is used to create a circular hole in the rib cage. A small incision is made between the ribs and the tip of the cutting tool is inserted between the ribs. A biopsy punch is slid over the rod and the tool pulled up through the center of the punch cutting a circular hole. B) A further example with dimensions indicated.
Figure 19B:
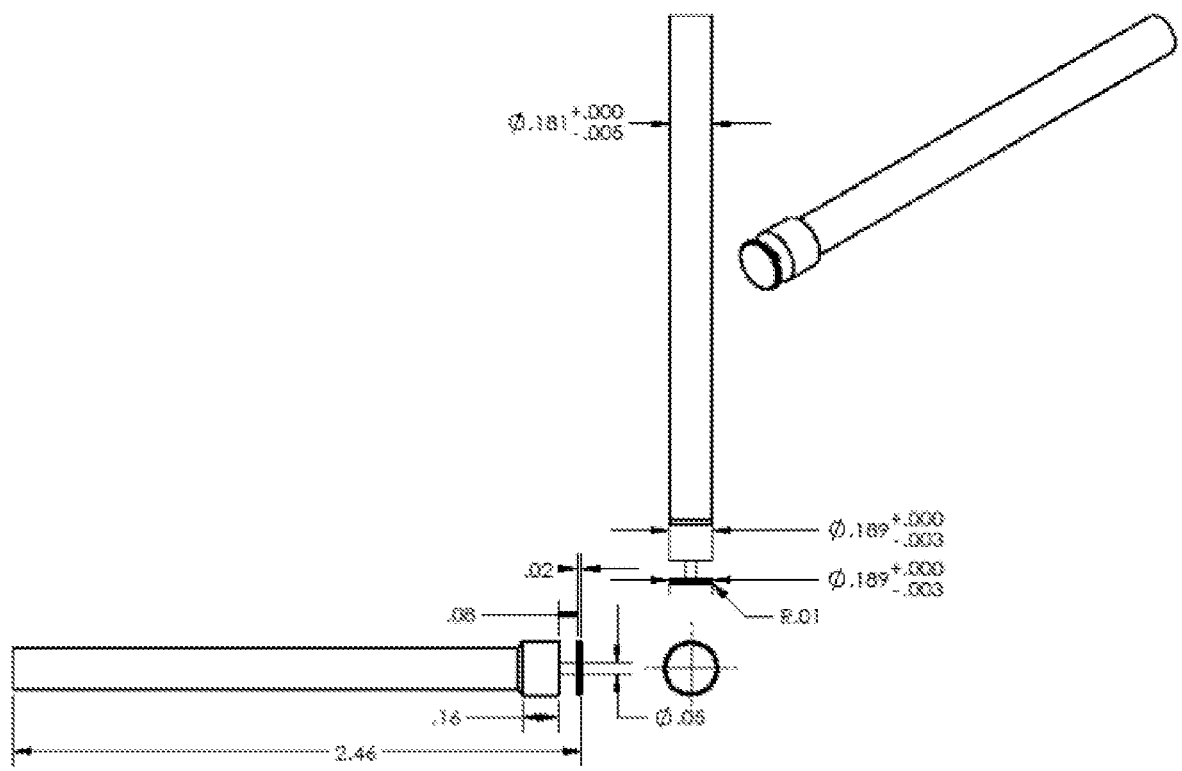
Figure 20A:
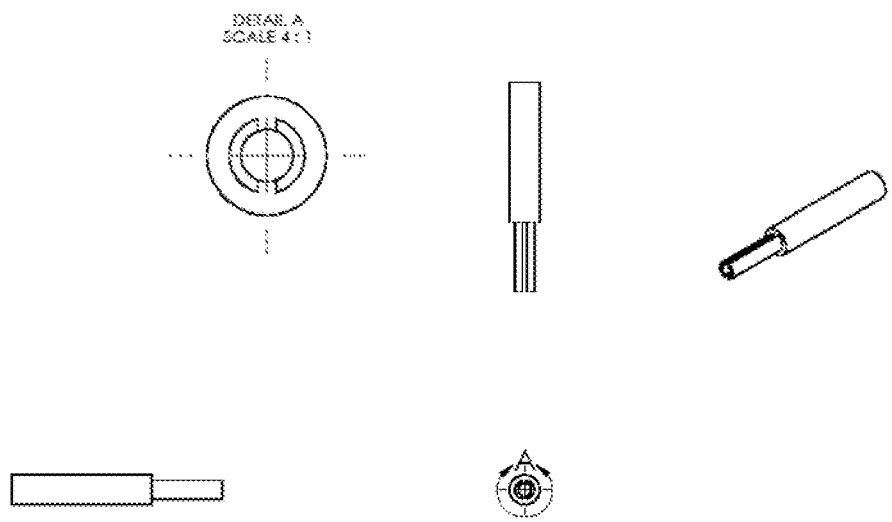
FIG. 20A-20B. Examples of a window frame holder tool. A) The tool is used during the lung window surgical protocol to aid manipulating the window frame during implantation. B) A further example with dimensions indicated.
Figure 20B:
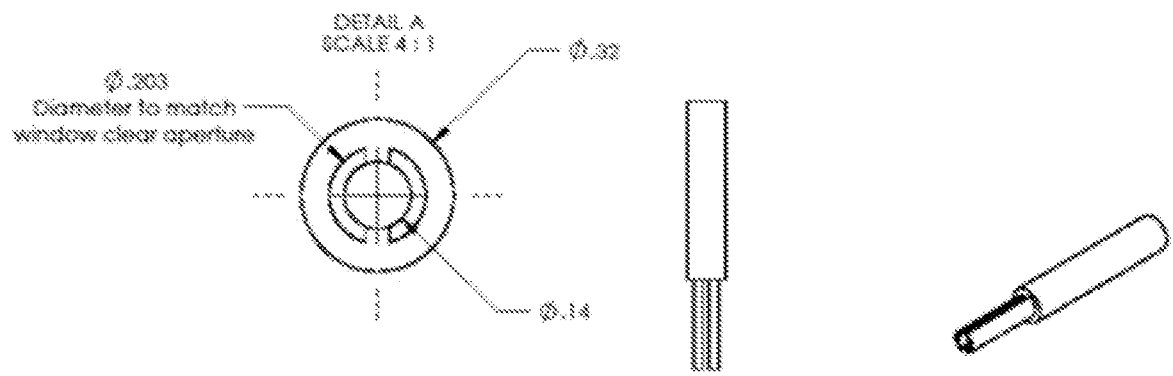
Figure 20B:
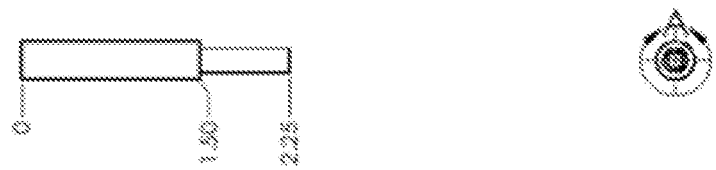

Preferably, the circular incision is made using the rib cutting tool illustrated in FIG. 19A or 19B. Preferably, the window frame has the structure show in FIG. 12A, 12B, 13A, 13B or FIG. 17. The window frame can be made of stainless steel that has undergone passivation prior to implantation of the window frame in the subject. Preferably, the window frame is manipulated into position using the window frame holder tool shown in FIG. 20A or 20B. Preferably, the window frame is secured using a suture that has been threaded between the adjacent ribs before the window frame is positioned in the incision. Preferably, the quick-setting adhesive is cyanoacrylate. Preferably, the fixturing plate has the structure shown in FIG. 12 C, 12D or FIG. 18. The fiducial marks on the window frame can serve as navigational reference points and, along with the xy stage origination, can form a set of vectors from which a coordinate transformation connecting repeated imaging sessions can be derived.

The methods disclosed herein can be used to visualize tumor cell movement, extravasation, tumor growth, tumor cell progression to metastases, or dynamics of interactions among cells including tumor cells, macrophages and endothelial cells, and subcellular dynamics including cell division, invasive protrusion and signaling secretion.

The microscope can be a confocal microscope and is preferably a multiphoton microscope.

Due to the tissue stabilization, images obtained by the methods disclosed herein do not require further processing to remove motion artifacts.

The subject can be any mammal, such as for example a laboratory animal, such as for example a mouse, rat, gerbil or rabbit.

The invention further provides a fixturing plate for holding a window frame for intravital imaging, wherein the fixturing plate has the structure shown FIG. 9A, 9B, 12C, 12D or 18.

The invention further provides a window frame for holding a window for intravital imaging, wherein the window frame has the structure shown in FIG. 12A, 12B, 13A, 13B or 17.

The invention further provides a window frame for holding a window for intravital imaging of a tissue of interest, such as the lung, in a subject, wherein the window frame comprises portions defining
  a beveled edge that rests against the tissue of interest,
  a groove into which a skin flap or ribcage fits, and
  a recess for the window.
The window frame can have the structure shown in FIG. 12A
wherein (1) illustrates a beveled edge, (2) illustrates the groove and (3) illustrates the recess for the window. The invention further provides a fixturing plate comprising portions defining a recess that accepts the window frame.

Figure 10A:
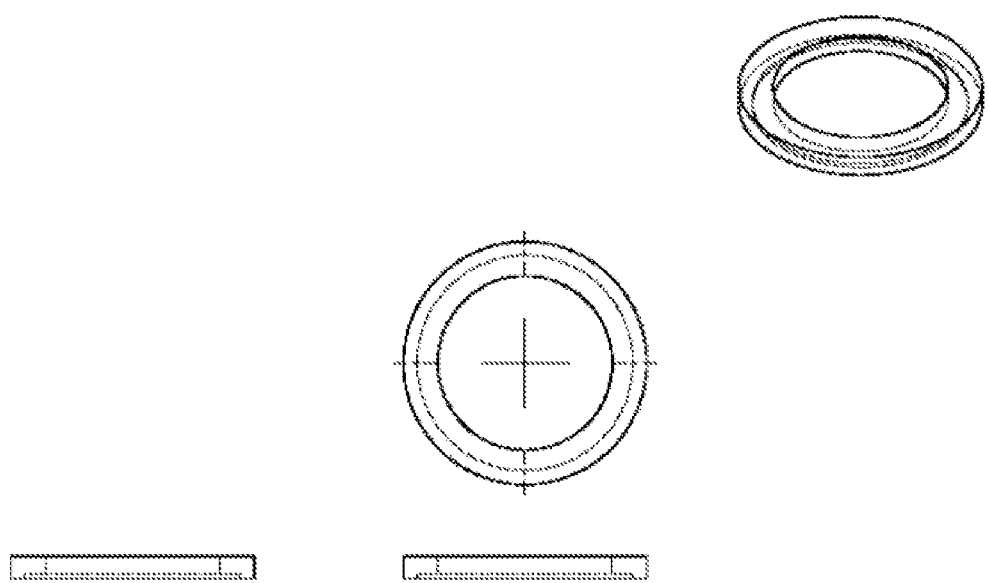
FIG. 10A-10B. Examples of shallow window design. A) A generalized example; B) a further example with dimensions indicated.
Figure 10B:
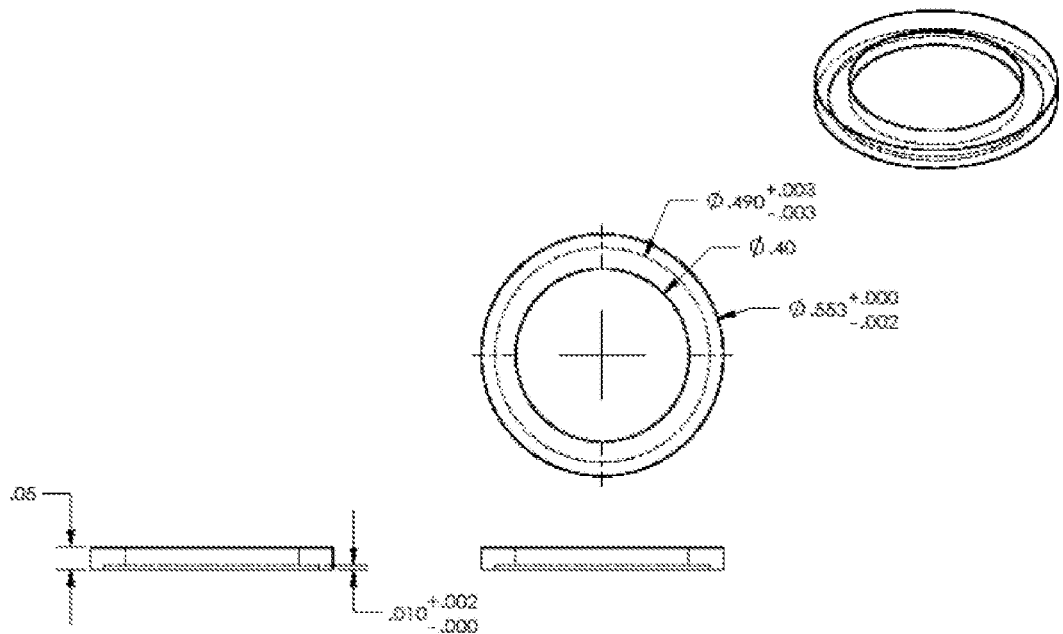

The invention further provides a window having the structure shown in FIG. 10A or 10B.

The invention further provides a kit for intravital imaging comprising one or more of the following:
  one or more fixturing plates,
  a window frame,
  a window,
  a rigid backing for tissue stabilization,
  a rib cutting tool, and
  a window frame holder tool.
The fixturing plate can have, for example, the structure shown in FIG. 9A, 9B, 12C, 12D or 18. The window frame can have, for example, the structure shown in FIG. 12A, 12B, 13A, 13B or 17. The window can have, for example, the structure shown in FIG. 10A or 10B. The rib cutting tool can have, for example, the structure shown in FIG. 19A or 19B. The window frame holder tool can have, for example, the structure shown in FIG. 20A or 20B.

The present invention provides a novel combination of mosaicked-stitched imaging with intravital microscopy of live tissues (LVHR-IVI) in combination with non-obvious techniques to remove motion artifacts (i.e., tissue stabilization by novel fixturing plates) associated with living tissue. Complete immobilization of the tissue relative to the objective lens for very long periods of time, as required for LVHR-IVI, and repeated imaging of the same animal over days to weeks, as required to follow changes in tissue architecture during development and disease progression by LVHR-IVI, cannot be achieved by previous methods. The present invention does not require a customized microscope or image analysis software, and is compatible with nearly all automated xy-stage equipped multiphoton or confocal imaging systems.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example A

Overview

The present invention provides a combination of stabilization techniques with mosaicked and stitched intravital imaging, resulting in a process termed Large-Volume High-Resolution Intravital Imaging (LVHR-IVI). In the present invention, many high-magnification, high-resolution images are acquired in a mosaic pattern and stitched together to produce a low-magnification image.

The invention discloses a method for combining LVHR imaging with intravital imaging to create Large-Volume High-Resolution Intravital Imaging or LVHR-IVI—obtaining large area, high-resolution imaging in living animals that combines the advantages of histopathologic analysis with the live dynamics of intravital imaging. The method is composed of both a surgical technique for exposing and stabilizing the tissue of interest, and for the acquisition with multiphoton microscopy of multiple high-magnification tiles that are stitched together to form a large-area, low-magnification image. Also provided, as examples, are designs for tissue stabilization tools.

The techniques presented are validated and make large volume intravital imaging accessible with a multiphoton or confocal microscope. These approaches are compatible with nearly all automated xy-stage equipped multiphoton or confocal imaging systems.

Materials and Methods

Experimental design. Key to the success of LVHR-IVI in living animals is tissue stabilization. This is accomplished by capturing the window in a tightly toleranced recess that is bored into a custom-made xy fixturing stage plate (FIG. 1B & FIG. 9).

Using this concept as a basis for the design, the present invention provides a method that is applicable to many different tissues, which includes compliant tissues such as the mammary fat-pad, lymph nodes, and liver, which are particularly challenging as they are extremely compliant and easily transmit motion and vibrations from the animal's involuntary movements. In addition, the invention extends the immobilization to many days making LVHR imaging possible for the first time.

Figures 11A, 11B, 11C, 11D, 11E, 11F, 11G, 11H:
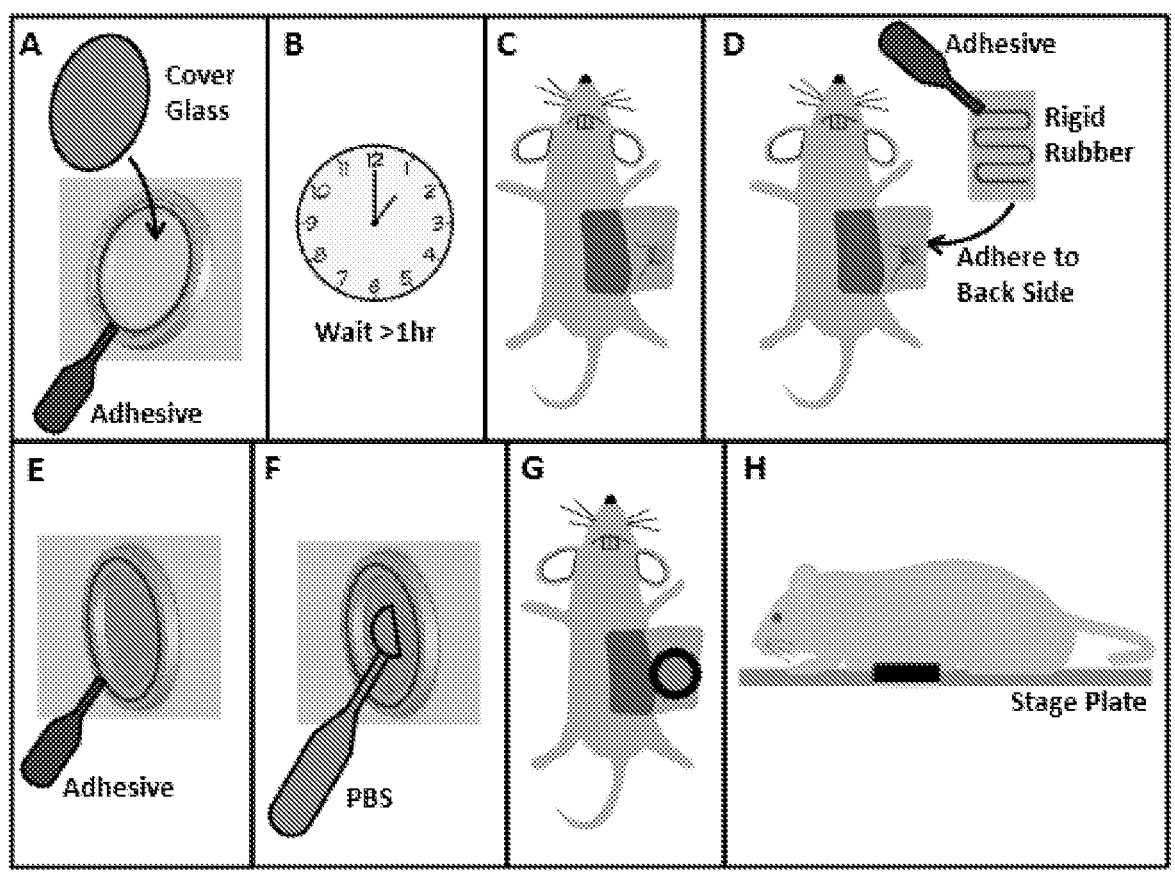
FIG. 11A-11H. Diagram illustrating the tissue stabilization method for compliant tissues. A) Preparation of the shallow imaging window. A thin layer of adhesive is placed on the inset rim of the window frame (line) and the cover glass seated in the recess. B) Waiting time for adhesive to completely set. A setting time of one hour ensures that the cover glass cannot become dislodged and forms a water tight seal. C) Surgical exposure of the tissue of interest. D) Stabilization of compliant tissue. The application of adhesive to a rigid piece of rubber allows it to be adhered to the back side of the tissue of interest. E) Application of adhesive to the frame of the shallow imaging window. Applying adhesive only to the rim of the imaging window (line) will stabilize the tissue within the window, while avoiding exposure of the tissue of interest to the adhesive. F) Application of PBS to the cover glass. Before applying the window to the tissue, a 2-3 mm droplet of PBS is suspended from the center of the cover glass. When sealed to the tissue, a hydration chamber is formed which prevents dehydration of the tissue. G) Mouse with window adhered. Once window is adhered over the tissue of interest, the mouse may be positioned on the microscope. H) Mouse positioned on microscope stage. To begin imaging, the mouse is inverted and the window placed into the recess in the fixturing stage plate.

The method begins with the surgical exposure of the tissue of interest. FIG. 1C demonstrates this using the mammary fat-pad or inguinal lymph node as an example location. Once surgically exposed, adhesive is applied to the underside of a shallow window frame holding a circular cover-glass (FIGS. 10, 11). A small droplet of PBS is placed in the center of the cover-glass and the window is positioned so that the tissue of interest is centered under the cover-glass (FIGS. 1D & 1E). Finally, as in FIGS. 1B & 11H, the animal is placed on the custom xy fixturing stage plate with the window inserted into the recess. The adhesive creates a seal surrounding the tissue of interest and keeps it moist, preventing dehydration. As was shown by Ritsma et al. (2012), the use of adhesive on the rim of the window does not impact the integrity and viability of the tissue within the imaging area.

Microscope setup. Many commercially available microscopes utilize multiple objective lenses; however, a single low-magnification, high-numerical aperture, long-working distance objective lens (25× 1.05 NA) is sufficient for nearly all imaging tasks. As discussed in Entenberg et al. (2015), this lens provides: the working distance needed for intravital imaging deep into tissues; rapid switching through a wide range of magnifications by utilizing electronic zoom; nearly the same resolution (~0.25 μm lateral and 1.3 μm axial) as high magnification water immersion lenses; and high light throughput across the entire visible and near infrared spectrum. While advantageous, this method does not, however, rely on utilization of this objective lens and can be performed with many different lenses. All of the images presented in this example are single optical slices acquired with this objective lens.

Similarly, while a custom designed multiphoton microscope (Entenberg et al. 2011) was used to generate these images, this procedure can be performed on any commercially available multiphoton or confocal microscope so long as it is equipped with an automated xy stage that is capable of recording a list of preset positions to acquire sequentially and hold the spatial fixturing plates for each of the different window designs (FIGS. 9-12).

Finally, many commercially available microscopes come with either the ability to automatically program their automated xy stage for mosaicked acquisition, or the ability to import collections of xy coordinates. An excel spreadsheet can be used to generate the list of coordinates for automated import. The easiest way to accomplish this is to use the stage controller software to export a list of manually selected coordinates. Using this file, one can determine the format for the output text file. This format typically consists of numbers for x, y, and z coordinates and some surrounding text. The text can be altered to match the output format for the stage controller. If all coordinates are located on a single output line, columns of the spreadsheet can be copied directly into a text file and uploaded into the stage controller after updating the imaging parameters.

Materials:
Fluorescent dyes such as Tetramethylrhodamine isothiocyanate-Dextran (T1287, Sigma-Aldrich), Evan's Blue (E2129, Sigma-Aldrich), or Texas Red Dextran (D1830, Thermo Fisher Scientific)
Phosphate Buffered Saline (PBS) (14190136, ThermoFisher Scientific Inc.)
Isoflurane (029405, Henry-Schein)
Anesthesia unit (100 Series Vaporizer, SurgiVet)
Charcoal Filters (F-Air CS, Braintree Scientific, Inc.)
Tubing (6516T14, McMaster Carr)
Oxygen supply (TechAir)
Transfer pipette (13-711-37, Fisher Scientific Inc.)
Puralube Vet Ointment (039886, Butler Schein Animal Health)
Petroleum Jelly (29704, Fisher Scientific)
Cyanoacrylate (1647358, Henkel Adhesives)
Transfer Pipette (13-711-37, Fisher Scientific Inc.)
Stiff rubber (1310N14, McMaster Carr)
12 mm #1.5 Cover-glass (72230-01, Electron Microscopy Sciences)
Pulse-oximeter (MouseSTAT, Kent Scientific)
Low magnification, high-resolution objective lens (XLPLN25XWMP2, Olympus)
Custom x-y fixturing stage plate with bored recess (e.g., FIG. 9) and
Custom shallow imaging window (e.g., FIG. 10).

General ethics statement. The procedures used in this example were carried out in accordance with the National Institutes of Health regulations concerning the care and use of experimental animals and with the approval of the Einstein College of Medicine Animal Care and Use Committee.

Mouse setup. Prior to starting the surgery, use cyanoacrylate to affix a cover-glass to the shallow window frame as shown in FIG. 11A. This should be done at least 1 hour before using the window to allow the adhesive to set (FIG. 11B).

Before beginning the surgery, prepare the microscope for imaging by turning on the imaging lasers and all electronics.

Turn on the anesthesia unit with a flow of 100% oxygen at a rate of 1.5-2 liters per minute mixed with 4-5% (vol/vol) isoflurane delivered to an anesthesia chamber. Place the mouse in the chamber. Take precautions to avoid inhalation of isoflurane during the procedure by using a well-ventilated room and a scavenging system. Activated-charcoal filters can be used to capture exhaust from the anesthesia chamber or from the ventilator. Runoff gas from the nose cone anesthesia unit can be removed using a suction hose connected to a ventilated house vacuum line.

Place the anesthetized mouse on the lab bench with a nose cone providing 100% oxygen mixed with 1.5-2% (vol/vol) isoflurane. The mouse's body temperature should be maintained at physiologic temperatures with an overhead heat lamp or a warming pad. Assure that the mouse is properly anesthetized by performing a toe-pinch test to determine the absence of the pain reflex before the start of the surgical procedure. If the animal withdraws in response, increase the dosage of isoflurane by 0.5%, wait for 1-2 min and repeat the toe-pinch test. Cover the animal's eyes with ophthalmic ointment to prevent drying since mice are unable to close their eyes under the influence of anesthesia.

Next, construct and insert an i. v. catheter following the procedure published by Harney et al. (2016). Avoid introducing bubbles into the catheter line, which can lead to air emboli and be fatal to the mouse. Administer 50-100 μL of sterile PBS via tail vein catheter to provide hydration during the surgical procedure. To prevent volume overload, be careful to not inject more than 200 μL. After the surgery, and during imaging, additional doses of ~50 μL per hour should be injected to maintain proper hydration of the animal.

Surgical procedure. To begin the surgical procedure, expose the tissue of interest through an appropriate sterile surgical technique (e.g., FIG. 11C). Several existing publications describe surgical protocols to expose various tissues including mammary tumors, (Entenberg et al. 2013, Harney et al. 2016, Wyckoff et al. 2011) and fat-pads (Harper et al. 2016), salivary glands (Masedunskas et al. 2013), liver (Dasari et al. 2015), lymph nodes (Liou et al. 2012, Sellers et al. 2011) and kidney (Dunn et al. 2007). These tissues fall into the category of compliant (e.g. mammary fat-pad, lymph node, salivary gland, etc.), which more readily transmit vibrations due to their jelly-like consistency, or rigid (mammary tumor, kidney, etc.) which are easier to stabilize due to their increased stiffness and inflexible shape. If the tissue is compliant, additional stabilization may be required.

This can be accomplished with a rigid backing formed by a small piece of stiff rubber, cut to just larger than the exposed tissue. Take the rubber, apply a thin film of cyanoacrylate to one face, and affix it to the back side of the tissue, as shown in FIG. 11D.

After the animal is placed on the stage and imaging is attempted, excess movement from breathing may be noted. This can be addressed by ensuring that the tissue connecting the imaged area and the body of the animal is not pulled taut and/or by applying gentle pressure (as described in the protocol by Masedunskas et al. (2013)) to the top surface of the tissue (or, in the case of compliant tissues, the rigid rubber backing that was glued to the tissue).

Next, take the shallow imaging window and apply a small film of cyanoacrylate to the window frame in the location indicated in FIG. 1E and FIG. 11E. Using a transfer pipette, apply a small droplet of PBS (~10-20 µL) to the center of the cover-glass on the side that will face the tissue (see FIG. 11F). Make sure that the PBS droplet on the cover-glass does not come into contact with the cyanoacrylate on the rim of the window as this will cause the cyanoacrylate to polymerize and set prematurely. The droplet should be ~2-3 mm in diameter. If made larger, the droplet may not cling to the cover-glass when transferred to the tissue or may contact the adhesive causing premature setting. Invert and center the window over the tissue of interest and gently press the window frame to the tissue to adhere (FIG. 11G). Make sure that the area of interest is kept in the center of the window and the surface of the tissue is relatively dry before attempting to adhere the window.

Mouse positioning on stage. Apply a thin layer of petroleum jelly to the bored recess on the underside of the fixturing stage plate. The petroleum jelly will form a hydrophobic barrier between the shallow imaging window and the fixturing stage plate preventing wicking of water between the two via capillary action. Snap the fixturing stage plate onto the xy stage. Transfer mouse and anesthesia unit to the xy stage.

Invert the mouse and set the shallow window into the bored recess (FIG. 11H). Be careful not to dislodge the window or the tail vein catheter at this time. Place environmental enclosure around the animal and turn on the heater. The tail vein catheter may be kept outside of the box for easy access. Using a transfer pipette, place a large drop of water between the objective and the cover-glass and visualize tissue by eye through the ocular. Verify that the vasculature of the tissue is perfused by observing flowing erythrocytes.

Crucial to the success of long term intravital imaging is the maintenance of the animal's proper physiology. As mice lose their ability to regulate body temperature under the influence of anesthesia, it is important to heat the animal with either a warming pad, or a chamber flooded with temperature-regulated forced air. Monitor the vitals of the mouse using a pulse-oximeter and adjust the isoflurane level to maintain a surgical plane of anesthesia.

Mosaic image acquisition. Position the xy stage at the upper-left-most corner of the area to be imaged and zero the xy stage controller. Using, for example, a Mosaic Creator Excel spreadsheet enter the size of the microscope's field of view, the desired number of x-tiles, y-tiles and field overlap. Upload the positions generated into the xy stage controlling software. Visit a sampling of the positions to see if the laser power and detector gains are set correctly for the tissue. Acquire images from all of the mosaic positions and save them to disk.

Data Analysis. There are multiple software packages that can be used for analyzing the acquired 3D and 4D data including commercially available packages Imaris® (Bitplane AG Corp.), Volocity® (PerkinElmer Inc.), and Amira® (FEI Inc.), and the freely available open source Fiji (NIH). While the choice of which software to use is based partly on personal preference and familiarity with a particular package, as well as availability, each does offer some advantage over the others. An excellent review of these and other software packages, along with highlights of some of their advantages and limitations is presented by Walter et al. (2010). One advantage to Fiji is the free availability of many plugins to accomplish common tasks and the capability of writing custom macros to automate repetitive tasks. One such macro can be used to stitch the individually acquired tiles together and create a 3D or 4D data set known as a Hyperstack for analysis. Once the images have been saved, use the macro to load the images into Fiji and stitch them together. Make sure to set the correct number of x-tiles and y-tiles in the macro. The macro may need to be altered to accommodate the image file naming scheme for different microscopes. Once the mosaic has been loaded and stitched together, the ROI Manager in Fiji can be used to toggle on and off an overlay showing the outline of each of the original acquired fields of view.

If the mosaic is acceptable, image acquisition can be continued and mosaic-z stacks or mosaic-z stack-time lapses can be captured and saved. After all of the images have been acquired and saved to disk, the 3D or 4D mosaic can be stitched together as a hyperstack in Fiji. Examine the mosaic for events and locations of interest for further study. One can proceed to perform further time-lapse imaging on just those specific regions to investigate events with a high temporal resolution.

The acquisition of large volumes of data takes a much longer time than acquisition of individual fields of view. For typical multiphoton or confocal microscopes with acquisition speeds of 1 frame per second (fps), a 10×10 mosaic takes ~100 seconds to capture. This is the time required for each z-slice. In typical applications, tissues are imaged to a depth of 100 µm with a step size of 5 µm between each z-slice (a sampling size sufficient to capture 15-20 µm diameter cells at greater than Nyquist conditions).

If time-lapse imaging is required in order to capture the cellular dynamics in a field, the total acquisition time for a single time point becomes on the order of 30 minutes. Balancing the conflicting need for resolution, large area, large depth, and speed will depend heavily upon the type of biological process that is being studied. 30 minutes per volume may be sufficient to capture slow events such as cellular division or collective migration of tumor cells, whereas extremely rapid events such as the visualization of calcium signaling or circulating immune cells may be addressed by capturing only one low-magnification, high-resolution image for the tissue at the beginning of the imaging session and using the single mosaicked image to inform which individual fields of view warrant further, high-speed, analysis. Processes such as tumor or immune cell motility in tissue fall in between and are best addressed by limiting the number of z slices to a maximum of 2 or 3. Of course, microscope systems with a much higher frame rate (Entenberg et al. 2004, 2006) (e.g. video rate systems running at ~30 fps) can dramatically reduce this acquisition time from 30 minutes to 1 minute per time point.

The large size of the data sets that result from LVHR-IVI are memory intensive (occupying upwards of several gigabytes) and can present a challenge to efficiently and quickly stitch and to store. These two issues are not of great concern as the constant reduction in cost of hard disk space and increase in speed of processors will greatly ameliorate these issues with time. There is also currently a push to address these issues in the field of digital pathology (Clunie et al. 2016, Deroulers et al. 2013).

Theory: Development of the protocol. Traditionally, intravital imaging has been considered to be a practice that requires specialized equipment (Entenberg et al. 2013, Zinselmeyer et al. 2008) and significant skill, leading it to be regarded as a "technically difficult" process (Cahalan et al. 2003). However, recent commercialization of the microscope instrumentation along with the development of numerous protocols (Entenberg et al. 2013, Harney et al. 2016, Masedunskas et al. 2013, Wyckoff et al. 2010) and surgical techniques (Dorand et al. 2014, Ritsma et al. 2012) have simplified the process to the point where it has become accessible to an ever increasing number of labs (Weigert et al. 2013). In many applications of intravital imaging, just a few fields of view (FOVs), randomly positioned within the tissue, are recorded. Since these FOVs represent a small minority of the total imageable tissue, the overall architecture and context of the tissue is lost. This concept is illustrated in FIG. 2A with a photograph commonly used in the image analysis literature.

Some of this loss of information can be successfully compensated for by greatly increasing the number of FOVs acquired and applying mathematical algorithms designed to extract complex or hidden relationships between imaged parameters (Gilgorijevic et al. 2014). In that work, new insights were developed into the mechanisms of metastasis by utilizing a support vector machine (SVM) algorithm (a nonlinear, multiparametric classification algorithm suitable for the analysis of systems with arbitrary distributions and/or non-linear parameters) to analyze hundreds of fields of view and dissect the microenvironmental conditions that are responsible for invasive tumor phenotypes (Gilgorijevic et al. 2014).

Figure 2B:
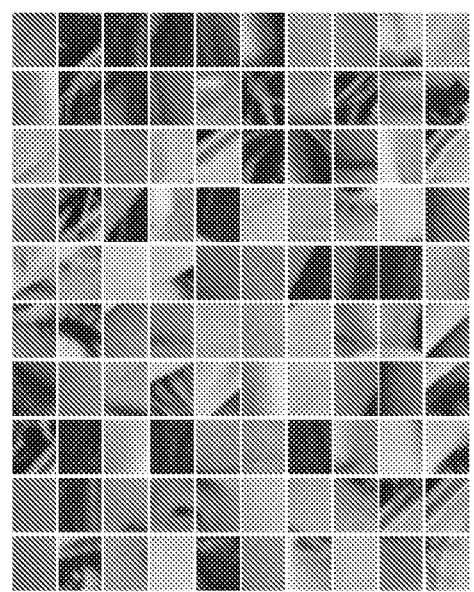
Figures 2C, 2D:

Though the large volume of data comprising the complete acquisition of all FOVs does give much more information about the underlying subject, a coherent picture is still lacking (FIG. 2B). What is missing in these studies is the reconstruction of the spatial relationship between the acquired fields. By acquiring the fields in a specific order and mosaicking them together (FIG. 2C) the spatial relationships of the images can be maintained and the overall architecture of the tissue reconstructed (FIG. 2D). This information may then be used to inform about the spatial ecology (identity, quantity and location) of the constituent components (cells, stroma, matrix, etc.) (Heindl et al. 2015, Kothari et al. 2013, Lloyd et al. 2015) or inform about which areas are most suitable for further analysis (e.g. time-lapse imaging).

While not common in the field of intravital imaging, mosaicking is a technique that has been used in multiple areas of research, such as biology, oceanography, and X-ray microscopy (De Zanet et al. 2016, Kwasnitschka et al, 2016, Loo et al. 2000, Price et al. 2006, Seshamani et al. 2006). It has even been combined with multiphoton microscopy, though only to image large areas of fixed and mechanically sectioned tissues (Price et al. 2006). Only one study in the published literature (Harper et al. 2016), an investigation into the mechanisms of early tumor cell dissemination from the mammary fat pad, has ever mentioned having utilized mosaic intravital imaging, albeit without reporting either the method or any mosaicked images.

Figure 3A:
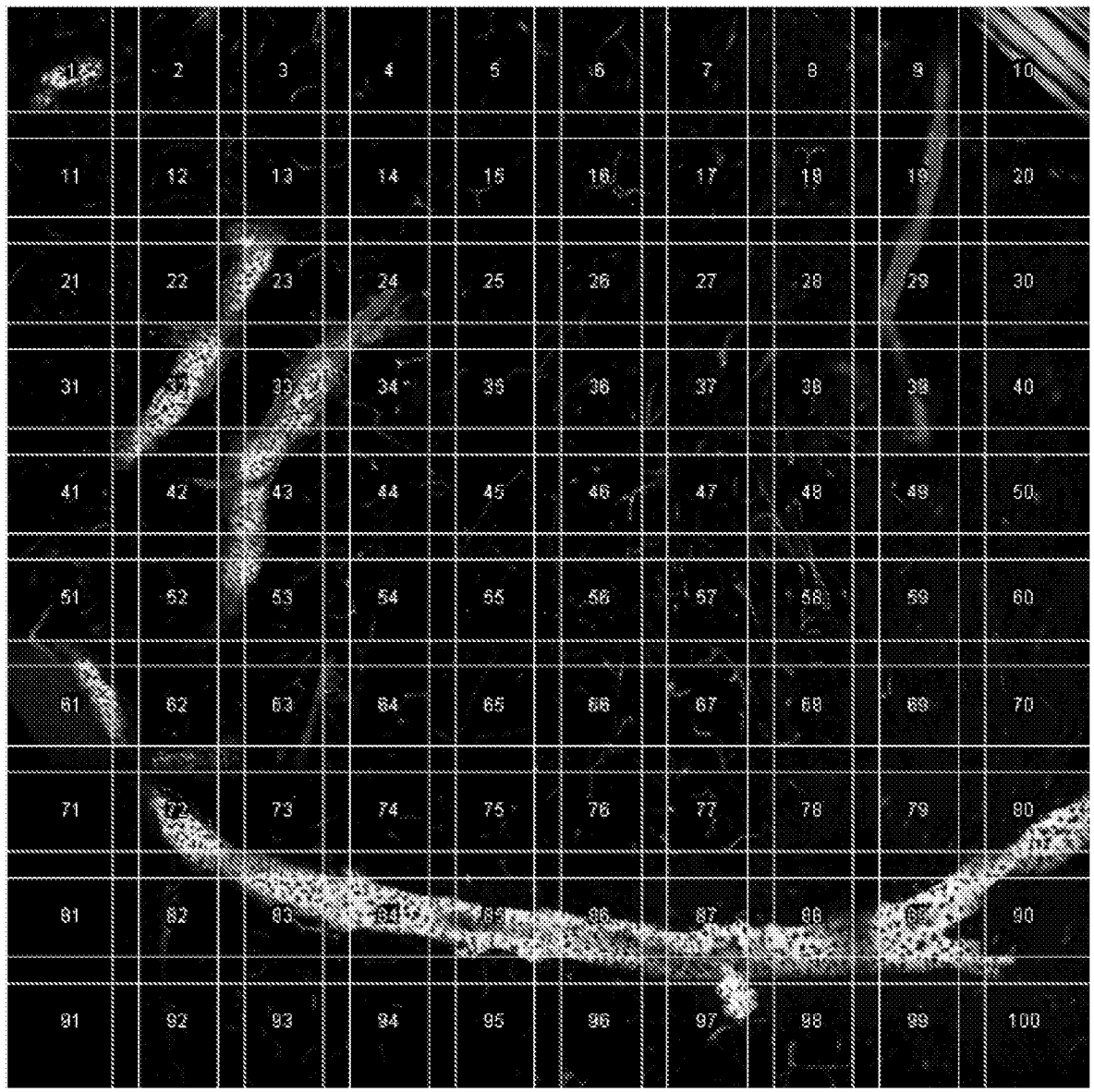
FIG. 3A-3C. Ordered acquisition and stitching of intravital images produces multi-scale, low-magnification, high-resolution images that provide histologic context to tissues while preserving single-cell resolution. A) A 10×10 mosaic of an untransformed fat pad in a 10 week old MMTV-Her2-CFP mouse whose mammary epithelia were transgenically labeled with CFP and vasculature labeled with fluorescently labeled dextran injected iv. Boxes show the outline of each acquired field of view and numbers indicate their order of acquisition. Fields of view are overlapped to compensate for non-uniform flatness of field illumination. FOV=2.1×2.1 mm. B) Stitched images show the overall structure of the tissue. The formation of the ductal tree by the epithelial cells is clearly visible as are the blood vessels that support them. Portion of the image in the box outlined near bottom is enlarged in C). C) A single lobule consisting of several acini can be observed budding off of the ductal tree. All panels: Optical resolution=250 nm.

Given the very sparse structure of the mammary ductal tree, LVHR-IVI proved crucial to the successful identification of regions for further high-resolution time-lapse imaging. Since this tissue is extremely compliant, however, intercostal muscle contractions produced significant motion artifacts, which were only overcome with the application of the techniques described in this method (shallow window and custom xy-fixturing stage plate). With the tissue stabilized, large areas were imaged with high-resolution by the serial acquisition of individual high-magnification high-resolution tiles, which were then mosaicked and stitched together. FIG. 3A shows an example of acquired fields of view (boxes) arranged in order along with the sequence of their acquisition (numbers). To compensate for non-uniform field illumination, the positions of the individual images are overlapped somewhat (10-20%). Depending upon the degree of non-uniformity in field illumination, dark bands may still be visible on the stitched images. Though not utilized in this work, optimized stitching algorithms may be used to further reduce these effects (Legesse et al. 2015).

Figure 3B:
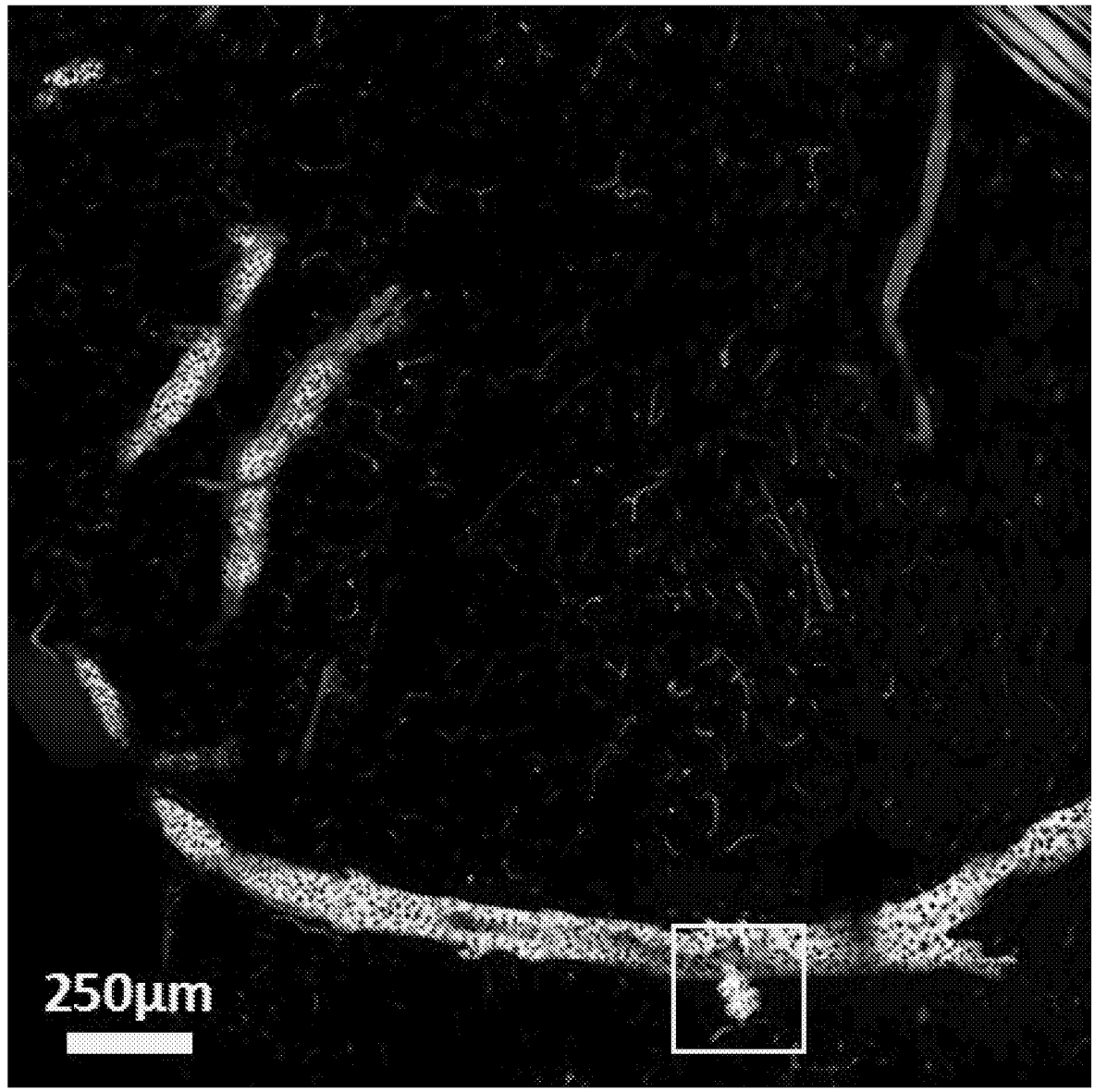
Figure 3C:
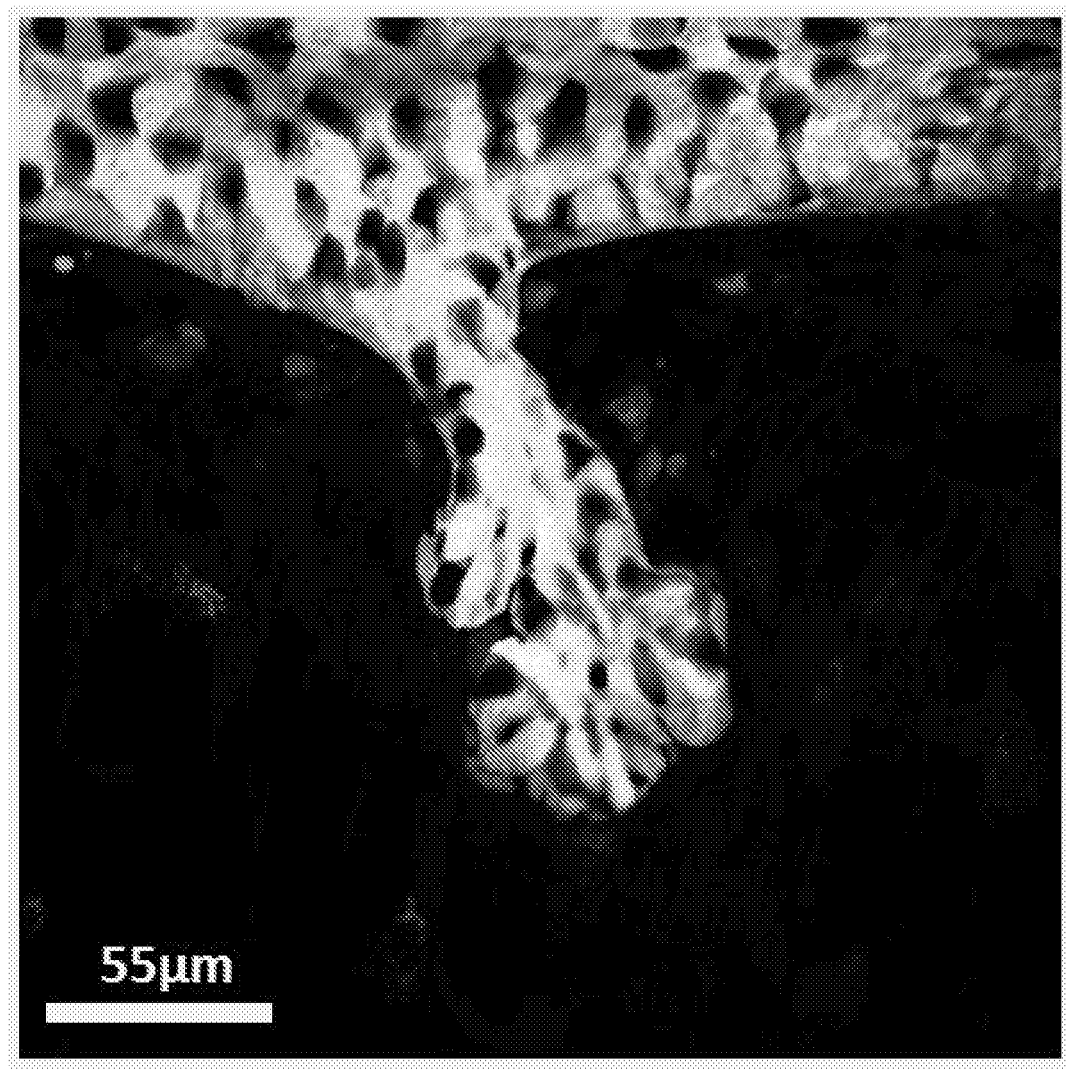

These mosaics thus provided a low-magnification view similar to those utilized by pathologists during initial histopathological assessment of tissues (FIG. 3B). This low-magnification overview is crucial for understanding the biological context of the imaged cells. For example, FIG. 3C shows a zoomed in image of the indicated area in panel B. In panel C the structure could easily be mistaken for a microinvasion of tumor cells into stroma. However, the low-magnification view in panel B reveals this structure to be a normal branching duct. The risk of this potential misidentification is high since malignant foci frequently overlap with benign structures. The low-magnification view provides essential information necessary to distinguish benign from malignant processes, and to identify regions of interest for further high-resolution time-lapse imaging.

Results

The invention presented here enables the combination of large-volume high resolution imaging with intravital microscopy. As such, it consists of two parts. The first part is a method for the acquisition of low-magnification, high-resolution intravital images built up by acquiring many individual, high-magnification tiles in a sequential manner and stitching them together. A prerequisite for the success of this method is the stabilization of the tissue of interest.

Figures 4A, 4B, 4C, 4D:
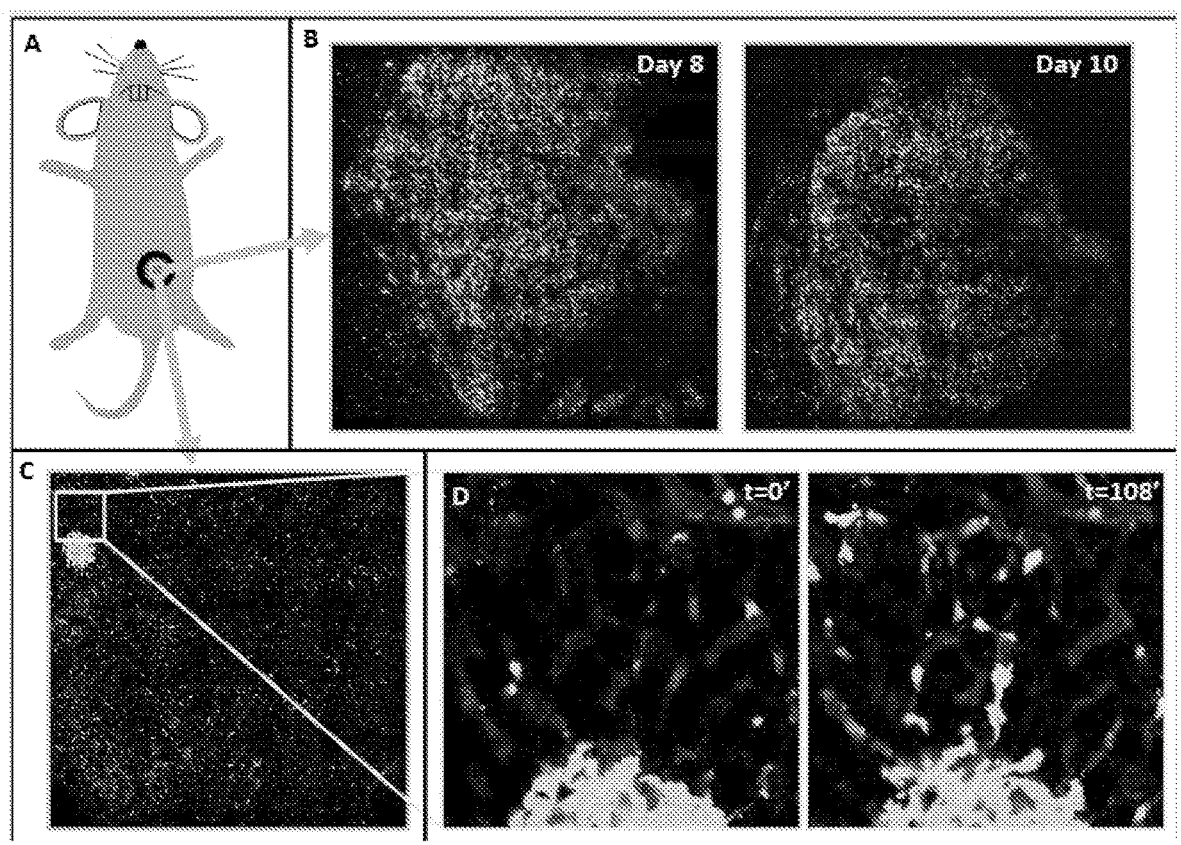
FIG. 4A-4D. Mammary and abdominal imaging windows provide sufficient tissue stabilization in order to perform mosaicking. A) Cartoon representing a mouse with an imaging window surgically implanted. B) 10×10 mosaics covering 2.8 mm of Dendra2 labeled MBA-231 orthotopic xenograft tumor implanted in the $4^{th}$ mammary fat-pad of a Rag2$^{-/-}$ mouse and imaged through a mammary imaging window on days 8 and 10 post-surgical implantation. C) 10×10 mosaic covering 1.4 mm of healthy liver tissue taken through an abdominal imaging window a C57/BL6 mouse whose myeloid cells were transgenically labeled with CFP (Ovchinnikov et al. 2008). Despite the low magnification, the high-resolution of the underlying fields of view is maintained. A collection of macrophages forming a granuloma-like structure can be seen. D) Stills from a subregion of the time-lapse mosaic shown in panel C showing single macrophages migrating out of the granuloma-like structure. FOV=170 μm. All panels: Optical resolution=250 nm.

Despite the large number of frame acquisitions, microscopes with a frame acquisition rate of just 1 fps can still capture time-lapsed, z-slice mosaics with a great enough repetition rate to capture single cell dynamics. This can be seen in FIG. 4C using an abdominal imaging window to view the liver. In this 10×10 mosaic covering 1.4×1.4 mm of liver tissue, a cluster of macrophages forming a granuloma-like structure can be seen. The vasculature has been labeled with high molecular weight (155 kD) tetramethyl-rhodamine (TMR), which does not leak out over time. Time lapse imaging of this tissue shows the dynamics of the macrophages. A subregion of the mosaic, focused on the collection of macrophages forming the granuloma-like structure (FIG. 4D) shows the motility of the single macrophages as they migrate out of the cluster.

Figure 5:
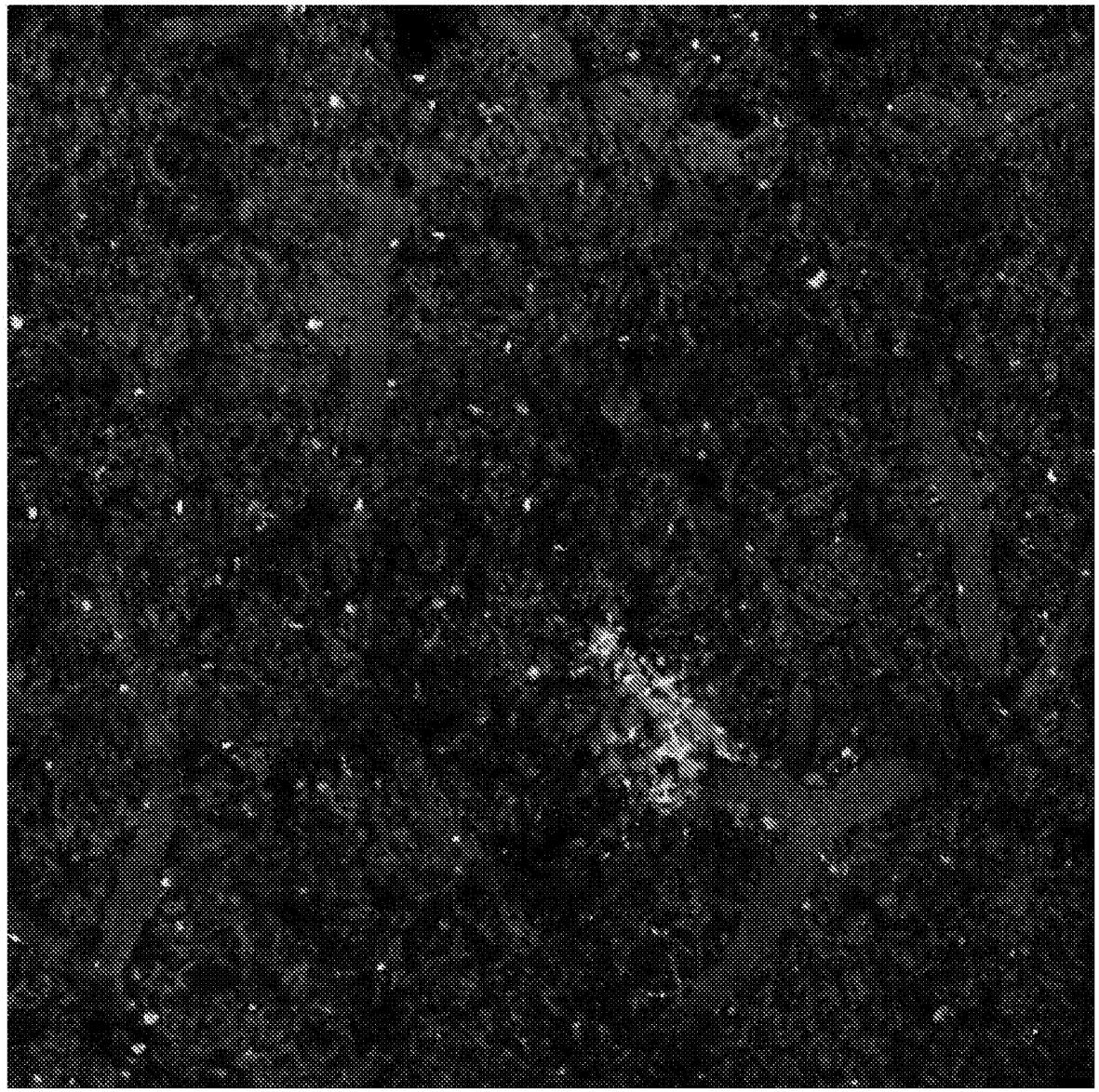
FIG. 5. Low-magnification, high-resolution, 6×6 mosaic of 1.2×1.2 mm of lung tissue containing a micro-metastatic lesion imaged through a vacuum-stabilized lung imaging window. The high mechanical stability provided by the vacuum-stabilized imaging window allows LVHR-IVI of E0771 tumor cells in the lungs of a C57/BL6 mouse whose myeloid cells were transgenically labeled with CFP (Ovchinnikov et al. 2008). Optical resolution=250 nm.

The mosaicking protocol was also performed with a vacuum stabilized lung imaging window (Entenberg et al. 2015, Roriguez-Tirado et al. 2016). The image stability of this technique is even sufficient to enable the use of the published blood averaging technique, which averages together all of the time points for the blood channel into a single image and then replicates this image as the background for each frame of the movie containing the other channels. This produces a clear view of the boundaries of the vasculature of the lung despite the numerous interruptions in vascular signal caused by the passage of unlabeled erythrocytes and leukocytes (Entenberg et al. 2015, Roriguez-Tirado et al. 2016) (FIG. 5).

Until now, there has not been a generalizable technique for the immobilization of living tissues, especially as these tissues become more compliant. As such, the second part of the invention presented here offers a generalizable procedure applicable to the stabilization of a range of tissue types and stiffness and over long periods of time (days to weeks).

Figures 6A, 6B, 6C:
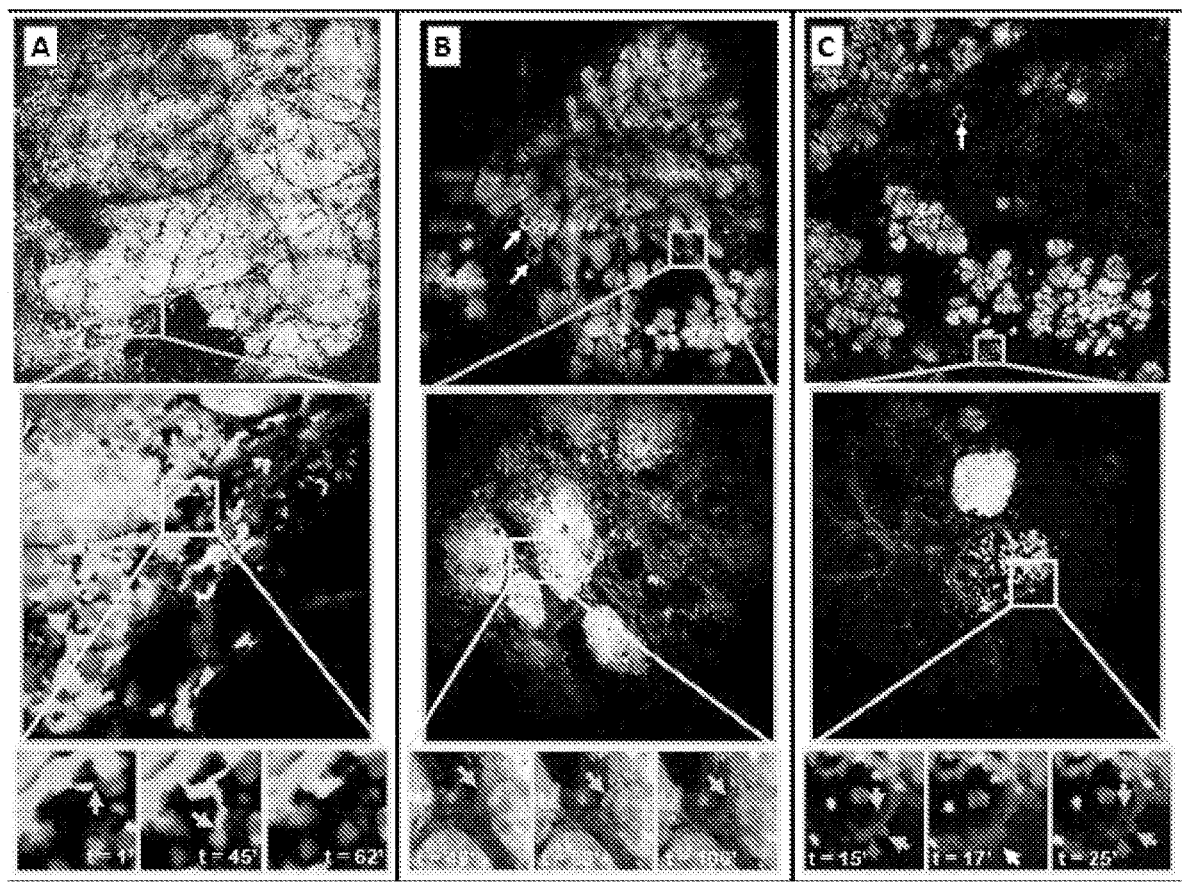
FIG. 6A-6C. Mosaic time lapse and z-series intravital imaging in transgenic mice allows acquisition of very large volumes of tumor heterogeneity that can be zoomed to follow single cell phenotypes in real time. A-C) Top panels: A single z plane showing large area imaging of a mammary tumor within a transgenic PyMT mouse expressing fluorescent proteins. Middle panels: One individual tile (indicated by squares) from which the mosaic is composed. Bottom panels: Time lapse imaging of the sub-region (indicated by squares). A) Top panel: 6×6 mosaic covering 1.6×1.6 mm of a late-stage carcinoma. Middle panel: Peritumoral region of local inflammation indicated by CFP positive myeloid cells located at the tumor-stroma interface. FOV=340×340 μm. Bottom panel: Stills from a time-lapse movie showing macrophages migrating to interact with tumor cells (arrows). FOV=60×60 μm. B) Top panel: 6×6 mosaic covering 1.6×1.6 mm of a few ducts undergoing hyperplastic changes (white arrows) and carcinoma showing areas of late (top) and early (bottom) stage. Middle panel: Region showing sheets of cancer cells with intersecting vasculature. FOV=340×340 μm. Bottom panel: Stills from a time-lapse of an intravasated tumor cell (arrow). FOV=60×60 μm. C) Top panel: 10×10 mosaic covering 4×4 mm of an early carcinoma. Middle panel: Image shows two groups of cancer cells with distinctly different growth patterns. FOV=512×512 μm. Bottom panel: TMEM (macrophage, tumor cell, endothelial cell in t=15' panel) induced transient vascular leakage (white arrow in t=17' panel). FOV=133×133 μm. TMEM remains after leakage has ceased at t=25'. All panels: Optical resolution=250 nm.

This generalizable procedure was used to image all stages of progression of transgenic mammary tumors. This includes the often imaged late-stage carcinoma (FIG. 6A), as well as the more challenging earlier stages including tissues with mixtures of late- and early-stage carcinoma (FIG. 6B), tissues with mixtures of early-stage and ductal-hyperplasia (FIG. 6C), and even the untransformed fat-pad (FIG. 3). In each of these cases, the low-magnification, high-resolution images generated by the method are able to be examined at single-cell resolution to identify regions of interest for further study. For instance, regions of macrophage infiltration were identified in the late-stage carcinoma (FIG. 6A, middle), and high-resolution time-lapse images of this region revealed tumor cells acquiring an invasive phenotype (FIG. 6A, arrows in bottom panels). In FIG. 6B, areas of tumor bed vascularization can be identified (FIG. 6B, middle) and the vasculature monitored to observe hematogenous dissemination of tumor cells (FIG. 6B, arrows in bottom panels). Finally, in FIG. 6C, low-magnification, high-resolution images of early carcinoma, a tissue traditionally unimageable intravitally due to its extreme compliance and instability, have been used to identify regions with distinctly different growth patterns (FIG. 6C, middle). High-resolution time-lapse imaging of these regions has captured the function of the micro-anatomical tripartite structure known as the Tumor Microenvironment of Metastasis (TMEM) (FIG. 6C, arrow in t=17' panel). TMEM consist of a tumor cell and perivascular macrophage in direct contact with an endothelial cell (blood vessel) and has been previously shown to act as sites of both cancer cell intravasation and transient vascular permeability (Harney et al. 2015, Karagiannis et al. 2017, U.S. Pat. No. 8,642,277 B2 issued Feb. 4, 2014).

Figures 7A, 7B, 7C, 7D:
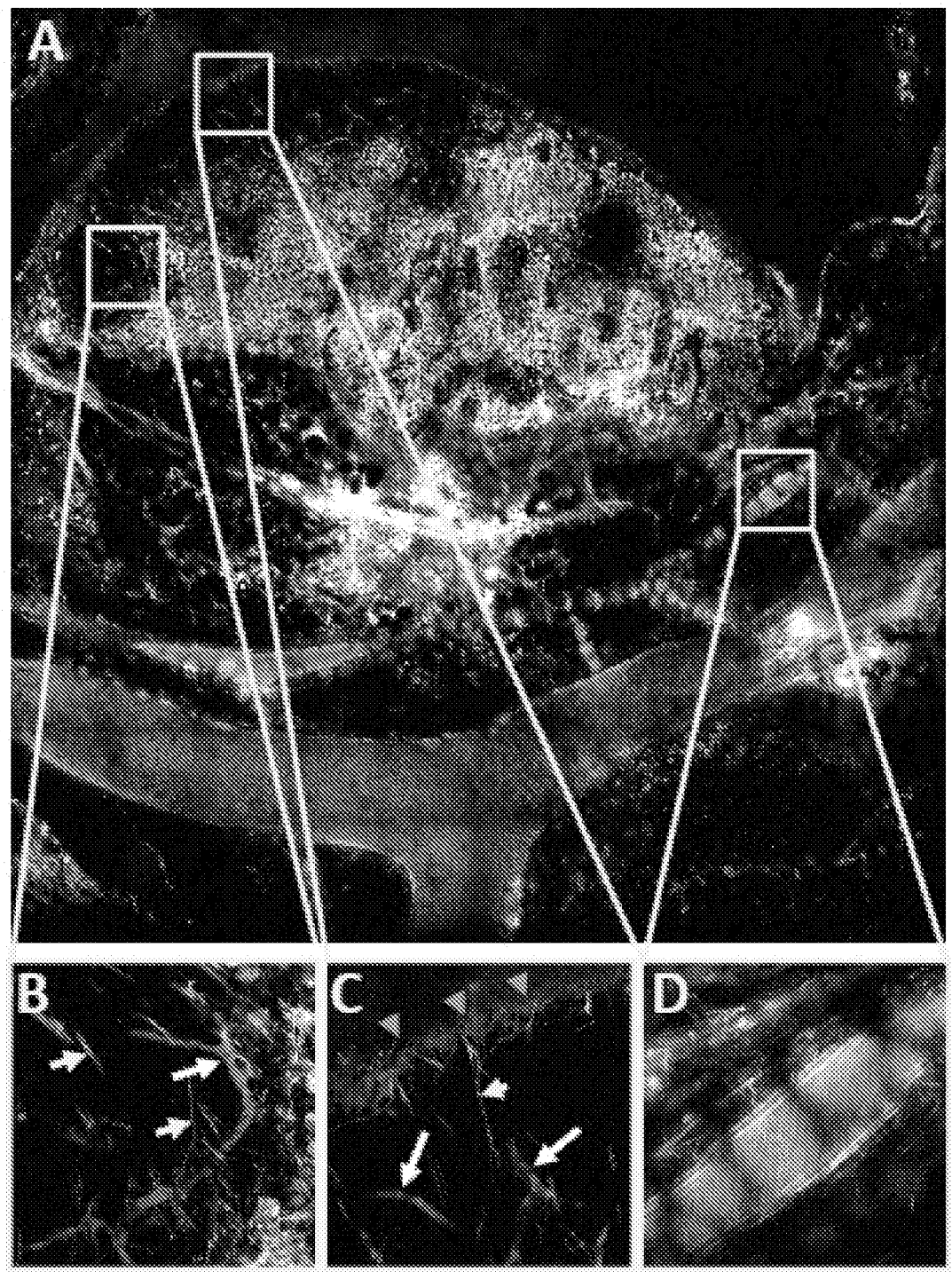
FIG. 7A-7D. Large scale mosaics reveal the structure and distribution of vessels and cells within compliant tissues such at the lymph nodes. A) 10×10 mosaic covering a 4×4 mm area of lymph node, blood vessels and lymphatics. B) and C) High resolution subfields showing subcapsular sinuses within the lymph node. Shadows of slow flowing erythrocytes (white arrows) and fine lymphatic capillaries (arrowheads) can be observed within these zones. FOV=300 μm. D) A high resolution subfield showing a fast flowing blood vessel external to the lymph node. FOV=300 μm. All panels: Optical resolution=250 nm.

In addition, both parts of the method presented here have been used to image the intact lymph node (FIG. 7). The low-magnification, high-resolution image (FIG. 7A) is an extremely useful guide for studies of the lymph node since its large extent (~3.5 mm) makes it very difficult to characterize the specific areas contained in any single field alone. This is demonstrated by the individual fields of view presented in FIGS. 7B-D. From any one of these fields of view alone, it is nearly impossible to determine if the imaged field is internal or external to the node or the identity of the structures. The context provided by the low magnification view clearly identifies panels B and C as sub-capsular sinuses with slow flowing capillaries (as evidenced by shadows of erythrocytes, white arrows) and fine lymphatic capillaries (arrows). Particularly difficult to identify without the low magnification overview is the lymph node capsule shown in panel C (arrows). Panel D demonstrates a fast flowing blood vessel traveling external to and alongside the node. The honeycomb shadow pattern is indicative of an overlaying layer of fat cells.

Figure 8:
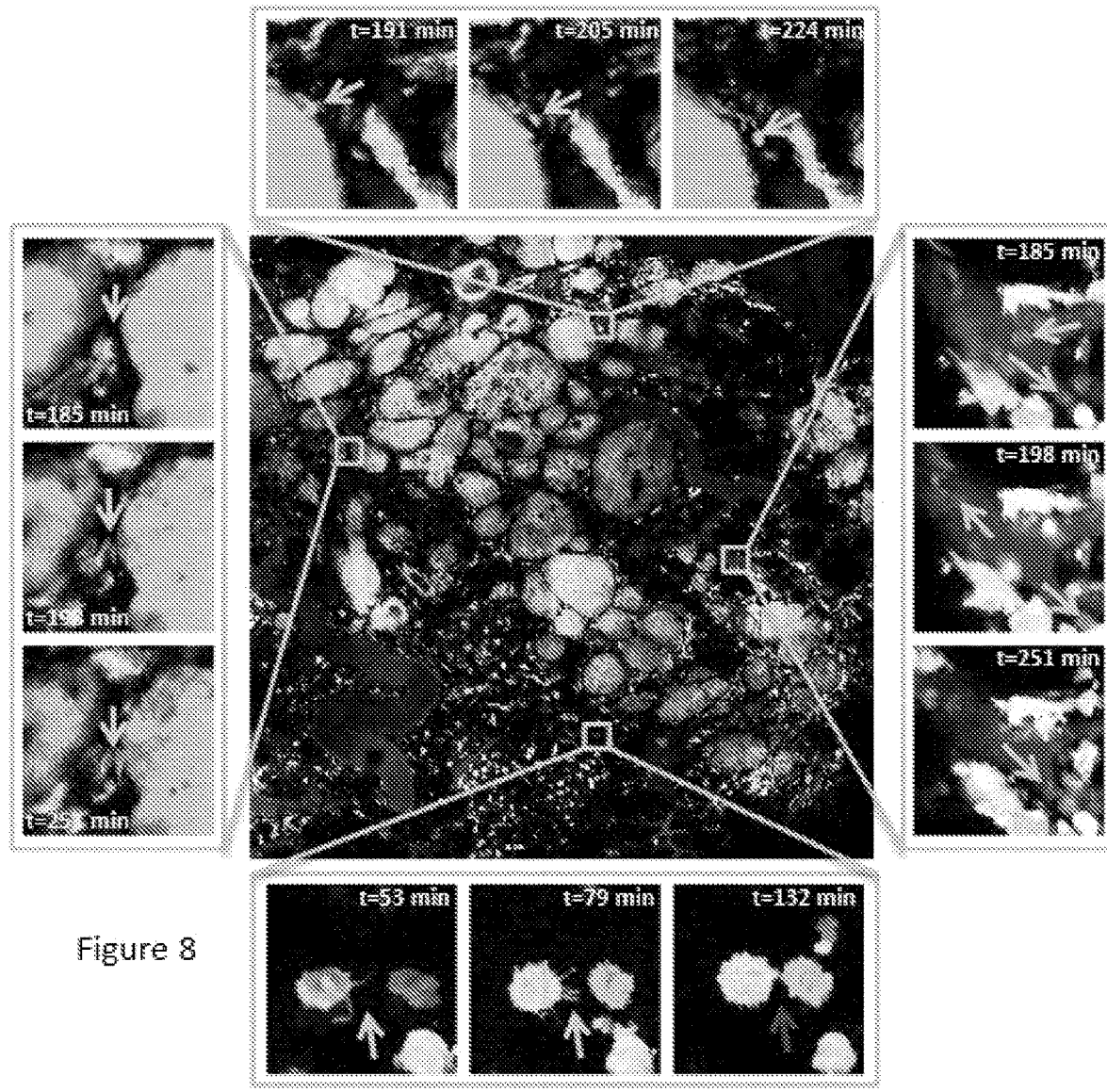
FIG. 8. Large-volume high-resolution intravital imaging captures time-lapse movies of large volumes of tumor tissue at single cell resolution and in real time. Center is a stitched mosaic of 36 (6×6) high-resolution image tiles taken of a transgenic PyMT tumor. Stills from simultaneously acquired sub-regions reveal single cell dynamics with subcellular resolution. Top: A chain of single tumor cells (arrows) can be observed separating from the main tumor and invading the stroma. Right: Individual tumor cells (arrows) can be seen in the vasculature. Left: A tumor cell protrusion (arrows) can be seen as the cell starts separating from the main tumor and moving toward macrophages. Bottom: As an example of the subcellular resolution of the imaging, an isolated macrophage can be observed extending filopodia (arrows) towards an isolated tumor cell. As the two cells make contact, the filopodia disappear (arrow). Field of View (FOV) of center image=1.6×1.6 mm. FOV of surrounding images=66 μm. All panels: Optical resolution=250 nm.
Figure 9A:
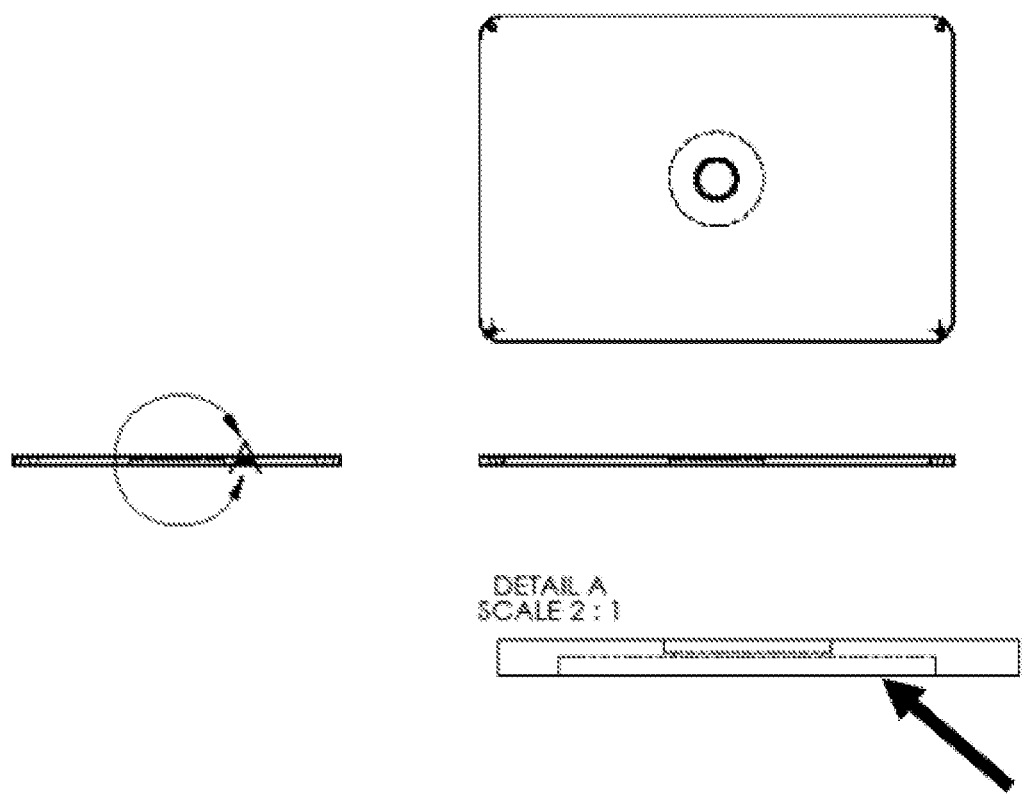
FIG. 9A-9B. Examples of XY stage insert design schematics. A) The XY stage plate features a tightly tolerance recessed groove (into which the imaging window inserts) and a recess which allows the objective lens to approach closely the inserted window (arrow). B) A further example with dimensions indicated.
Figure 9B:
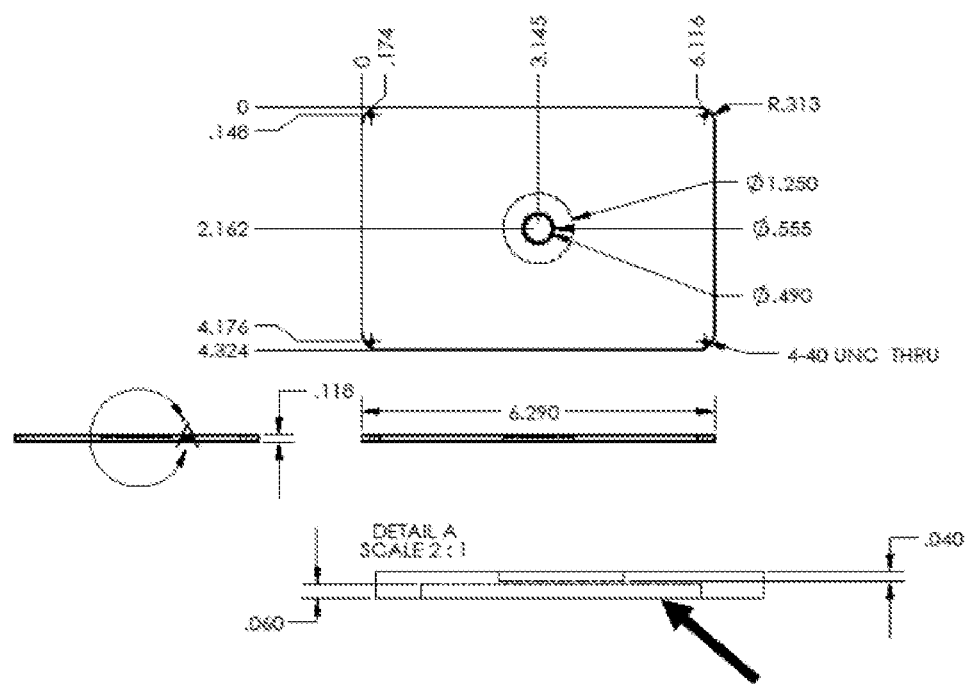

Finally, the time-lapsed LVHR-IVI allows the simultaneous capture and evaluation of the dynamics of the entire tissue. These time-lapsed multiscale images can allow a much more complete investigation of cellular dynamics than is possible with ordinary intravital imaging. FIG. 8 shows time-lapse LVHR-IVI of an entire tumor that is a mixture of early and late carcinoma. Careful examination of the images at high resolution reveals many processes occurring simultaneously including: single cell migration (FIG. 8, top); circulating tumor cells (FIG. 8 right); tumor cell-macrophage interactions (FIG. 8, bottom); and tumor cell invasion into stroma (FIG. 8, left).

Discussion

Intravital imaging (IVI) allows for a unique look at living tissue where the dynamics of individual cells can be directly observed and recorded in health and disease. This is accomplished through a combination of multiphoton microscopy's ability to perform non-destructive optical sectioning deep into thick tissues, with the ability to label the structure and function of cells and whole tissues using fluorescent dyes and genetically encoded fluorescent proteins. This combination produces images of the live tissue similar to those generated by mechanical sectioning and staining of fixed tissues.

While the acquisition of LVHR images of organs or tissues is straightforward when motion of the sample is not present, intravital imaging involves imaging a living animal, which imparts to the tissue many motion artifacts arising from breathing, heartbeat, and tissue dehydration. Thus, the limitation to successful combination of LVHR imaging with intravital imaging lies not in the microscope hardware or instrumentation, but in the ability to stabilize the living tissues sufficiently. While this is true for ordinary high-resolution microscopy, where motion artifacts on the order of microns can distort and destroy an image, it is even more crucial for mosaic imaging where stability requirements are exceedingly stringent given the extended time scale of the imaging.

The live multiscale view generated by these techniques allows for a better understanding of cellular dynamics in the context of the overall tissue architecture, guides the selection of regions for further high-resolution imaging and provides data on large volumes of tissue that can be analyzed using machine learning algorithms (Gligorijevic et al. 2014).

To make this combination of LVHR imaging and IVI feasible, new approaches for the stabilization of tissues have been developed. By combining these techniques with an imaging window, these studies can be extended over multiple imaging sessions spanning days to weeks. This enables the capture of events spanning orders of magnitude in space and time and directly addresses the restrictions of inadequate resolution and limited imaging periods that have precluded "the direct detection of slow processes, such as collective invasion with structural ECM degradation and remodeling that develop over days" (Friedl et al. 2012). The method presented here is a generalizable technique for the stabilization and large volume intravital imaging of living tissues. It is compatible with many types of tissues where cells and other structures of interest have been labeled using either genetically encoded fluorescent proteins or injectable fluorescent dyes. This method does not require a specialized microscope and can be accomplished with a multiphoton or confocal microscope equipped with an automated xy stage and controlling software. The images produced by this method are already stabilized and as such they do not require data processing to remove motion artifacts.

Example B

Overview

Stable, high-resolution, single-cell intravital imaging of the lung has recently become possible through the utilization of vacuum-stabilized imaging windows. However, this technique is extremely invasive, the vacuum generates artifacts in tissue dynamics due to vacuum-induced irregular blood flow, and it is limited to only hours in duration. To overcome these limitations, a Window for High Resolution Imaging of the Lung (WHRIL) is provided, which allows repeated optical imaging over a period of days to weeks without the need for mechanical ventilation (Looney et al. 2011), high-speed gated imaging (Vinegoni et al. 2014), or complex image processing post acquisition (Presson et al. 2011). The technique creates a "transparent ribcage" that seals the thoracic cavity and protects the lung tissue, allowing the mouse to recover completely and return to normal activity after surgery, and between each imaging session. This window produces the same high-quality images as vacuum stabilized windows without the vacuum-induced artifacts, while being less invasive and allowing imaging of the same lung tissue over a period of weeks. To easily and reliably relocalize the same micro-vasculature day after day, a technique known as microcartography (Dunphy et al. 2009) was adapted to this window.

The utility of the WHRIL is demonstrated by looking at multiple stages of metastatic progression of breast cancer, using both commonly employed experimental (tail vein injection), as well as the more clinically relevant spontaneous metastasis models, the latter of which has not previously been examined with intravital imaging due to the inability to determine when tumor cells arrive to the lung vasculature. Using these models, one can visualize all stages of metastatic disease, including tumor cell arrival, extravasation, growth, and progression to micrometastases, as well as Tumor MicroEnvironment of Metastasis (TMEM) function, the hallmark of hematogenous dissemination of tumor cells.

Materials and Methods

Animal Models. All studies involving mice were carried out in accordance with the National Institutes of Health regulation concerning the care and use of experimental animals and approved by the Einstein College of Medicine Animal Care and Use Committee. Two transgenic variants of the C57BL/6 strain of mice were used for intravital imaging, 1) a VeCad-tdTomato mouse expressing the fluorescent protein tdTomato on all endothelia generated by crossing B6.FVB-Tg(Cdh5-cre)7Mlia/J (006137, Jackson Labs) with B6.Cg-Gt(ROSA)26Sortm14(CAG-tdTomato) Hze (007914, Jackson Labs), and 2) a VeCad-tdTomato/ Csflr-ECFP mouse expressing tdTomato on endothelia and ECFP on macrophages generated by crossing the VeCad-tdTomato with Csflr-GAL4VP16/UAS-ECFP (Ovchinnikov et al. 2008). Once strains were established, all mice were bred in house. Only female mice between 12 and 36 weeks of age were used for experiments.

Validation. WHRIL bearing mice were visually observed daily for 14 consecutive days to determine reactivity to handling, appearance, and behavior based upon a previously published grading scale (te Velde et al. 2003). Each mouse was additionally weighed prior to window implantation and daily thereafter. Blood samples were obtained using retro-orbital collection pre-operatively and on 5 subsequent occasions and analyzed on a hematology analyzer (Forcyte, Oxford Science). A few measurements (8 of 48, <2 per animal) were lost due to clogging of the hematology analyzer.

WHRIL Surgery. Mice were anesthetized using 5% isofluorane (#029405, Henry Schein, Inc.) and surgery performed under aseptic conditions. Once anesthetized, the hair on the left thorax of the mouse is removed using a depilatory cream (Nair, Church & Dwight Co., Inc.). The mouse is intubated following the protocol of DuPage et al. (2009) using a 22 gauge catheter (#26746, Exelint International) that is then secured around the snout with 2-0 silk suture (Perma-Hand Silk LA55G, Ethicon Inc.). Placing the mouse in the right decubitus position on an operating surface and securing the limbs cranially and caudally with paper tape, the catheter is then connected to a mechanical ventilator (MouseVent for PhysioSuite, Kent Scientific Inc.). Anesthesia is reduced to 2% and the surgical field disinfected with 70% ethanol. A 1 cm diameter circular incision is made through the skin 7 mm lateral of the sternum and superior to the last floating rib.

The mammary gland and underlying muscle are excised using blunt micro dissecting scissors (RS-5980, Roboz) and electrocautery (GEM 5917, Braintree Scientific) when necessary to maintain hemostasis. A 5 mm circular hole is cut through ribs 6 & 7, taking extreme care not to touch the lung tissue. A purse string suture (774B, Ethicon, Inc.) is run 1 mm from the edge of the circular hole, intercalating between the ribs, and the stainless steel window frame is inserted so that the ribs and suture fit snugly into the 1.25 mm groove (see FIG. 12). The suture is tied three times with the knot fitting within the groove. Care must be paid not to cinch the suture too tightly as the muscle is delicate and tears easily.

Using small curved pickups (RS-5135, Roboz), the window frame is raised to separate the chest wall from the lung tissue allowing a small amount of cyanoacrylate (LOC1363589, Henkel Adhesives) to be dispensed on the underside of the window frame with an insulin syringe. By increasing the ventilator's positive end expiratory pressure (PEEP), the lung tissue is inflated so as to make contact with the underside of the window frame. PEEP is briefly held (~10 seconds) to allow the adhesive to set and then released. Next, PEEP is again briefly increased while a 5 mm, #1.5 circular coverslip (72296-05, Electron Microscopy Sciences) coated with a thin layer of cyanoacrylate glue is affixed on to the window frame and lung surface. Use of PEEP to inflate the lung ensures the window will adhere evenly over the entire surface.

Another purse-string suture is run through the dermis, cinching the skin under the frame of the window, and is secured with three knots, providing complete surgical closure. Finally, excess air within the thoracic cavity is evacuated using an insulin syringe placed through the diaphragm just below the xiphoid process and angled cranially towards the left shoulder. At the end of the surgical procedure, mice are allowed to recover from anesthesia, extubated, and buprenorphine (NDC 0409-2012-32, Hospira) is administered subcutaneously daily for pain control.

Microcartography. Prior to window implantation, window frames were etched with fiducial marks spaced 120 degrees apart using a carbide-tipped electric engraving pen. After implantation, each time the mouse was placed on the xy stage, the xy coordinates of these navigational reference points were located by moving the objective lens so as to image each etched line and the xy coordinates reported by the stage controller noted. The xy coordinates of each region of interest (ROI) were also noted and all coordinates were manually entered into the custom written microcartography software (LabVIEW, National Instrument, Inc.) which then calculated the coordinate transformation and applied the transformation to the ROI coordinates. This generated prediction coordinates for the regions of interest.

Window Passivation Method. Passivation of the steel ensures that the window is sterile at the time of implantation and remains inert over the duration of use. Passivation is a crucial finishing step that transforms the stainless steel to an inert material that can be safely implanted into the animal, preventing corrosion and subsequent inflammatory responses.

The protocol used for passivation is an acid-alkaline-acid (A-A-A) method, which was adopted from standards published by the American Society for Testing and Materials (ASTM A967-13) and the online protocol published by DeBold and Martin in 2003 (worldwideweb.mmsonline.com/articles/how-to-passivate-stainless-steel-parts). Briefly, after washing in a 1% solution of enzyme-active detergent (Terg-A-Zyme, Alconox Inc.), window frames are soaked for 30 minutes in a 5% solution of sodium hydroxide at 70° C. to 80° C. followed by a thorough rinse in tap water. Next, window frames are immersed for 10 minutes in a 7% by-volume citric acid solution at 50° C. to 60° C. again followed by a thorough rinse in tap water. The frames are again immersed in the sodium hydroxide solution for another 30 minutes and followed by a final rinse in tap water.

Intravital Imaging. Mice are anesthetized using 2% isofluorane and injected with dextran retro-orbitally for visualization of blood flow. For long time-lapse imaging sessions, a tail vein catheter is inserted following the protocol published by Harney et al. (2015) for periodic hydration using PBS and readministration of dextran. To stabilize the motion of the window, a thin fixturing plate (FIG. 12C) is placed between the skin and the outside lip of the window frame. The mouse is inverted, placed on the microscope stage and the fixturing plate is taped to the stage using paper tape. An environmental enclosure maintains the mouse at physiological temperatures and vitals are monitored using pulse oximeter (MouseStat for PhysioSuite, Kent Scientific). Imaging is performed on a custom built, two laser multiphoton microscope described previously (Entenberg et al. 2015, 2011). All images were captured in 16 bit using a 25×1.05 NA objective lens and acquired with 2 frame averages.

TMEM Imaging. To image the dynamics of TMEM function in the lung, mice were prepared following the Spontaneous Metastasis Preparation. Lung metastases that were greater than 200 μm were time-lapse imaged.

Cell culture. E0771-EGFP medullary breast adenocarcinoma cells, originally isolated from a spontaneous mammary tumor in C57BL/6 mice, were obtained indirectly from Dr. E. Mihich's lab at Roswell Park Cancer Institute, Buffalo, N.Y. Cells were cultured in RPMI medium 1640 (11875-093, ThermoFisher, Inc.) media as a monolayer. Cells were authenticated using exome gDNA sequencing to look at the single nucleotide variants for this line. Based upon the presence of three mutations, a homozygous activating K-Ras mutation, a truncating mutation and a non-synonymous SNV in p53, the identity of this cell line has been established. Cells were tested for mycoplasma contamination before use.

Experimental Metastasis Preparation. Cells for experimental metastasis were prepared by trypsinizing a 10 cm confluent culture dish of E0771-EGFP cells and passing them through a 40 μm cell strainer (352340, Falcon) to isolate single cells. Cells were then resuspended to a concentration of 1 million E0771 in 100 μL of PBS and injected into WHRIL bearing mice, post-operative day 1, via lateral tail vein.

Spontaneous Metastasis Preparation. Cells for the spontaneous metastasis models were prepared by injecting 1 million cells prepared as above in 200 μL of PBS into the right, fourth mammary gland. In order to best forecast when the WHRIL should be implanted in order to visualize lung metastases, tumor growth curves were established by injecting approximately $1\times10^6$ tumor cells into the right $4^{th}$ mammary gland of the mouse. Primary breast tumors were allowed to grow to a maximum of 2 cm over the course of 6 weeks. Two mice were sacrificed each week and their lungs excised and examined on a fluorescence microscope. The growth of micrometastases was evaluated by counting the number of single cells and micro metastases observable on the surface of the left lung. Using this information, it was determined that optimal time for observation of the initial arrival of tumor cells to the lung was 3-4 weeks, and the optimal time for observation of TMEM function was 4-6 weeks. In all cases, a WHRIL was placed 24 hours before imaging.

Figures 16A, 16B:
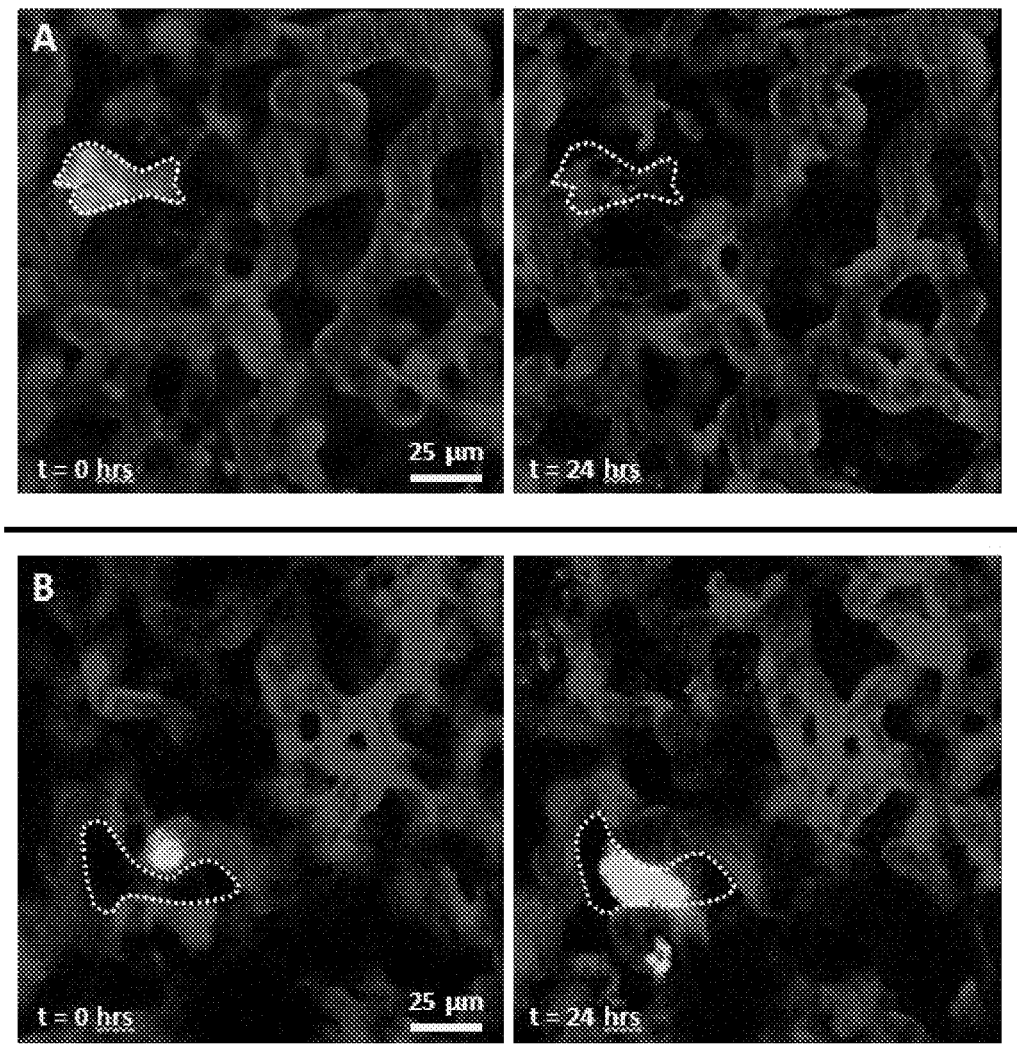
FIG. 16A-16B. Relocalization using microcartography enables identification of tumor cell fate between imaging sessions. A&B) Left: Image of a tumor cell trapped in the vasculature on POD 1. Right: Image of the same field of view relocated using microcartography 24 hours later. A) The tumor cell (white dotted outline) can be seen to have left the field of view either by recirculation or apoptosis. B) The tumor cell can be seen to have crossed the endothelium into the extravascular space (dotted outline). All panels: Optical resolution=250 nm.
Figure 17:
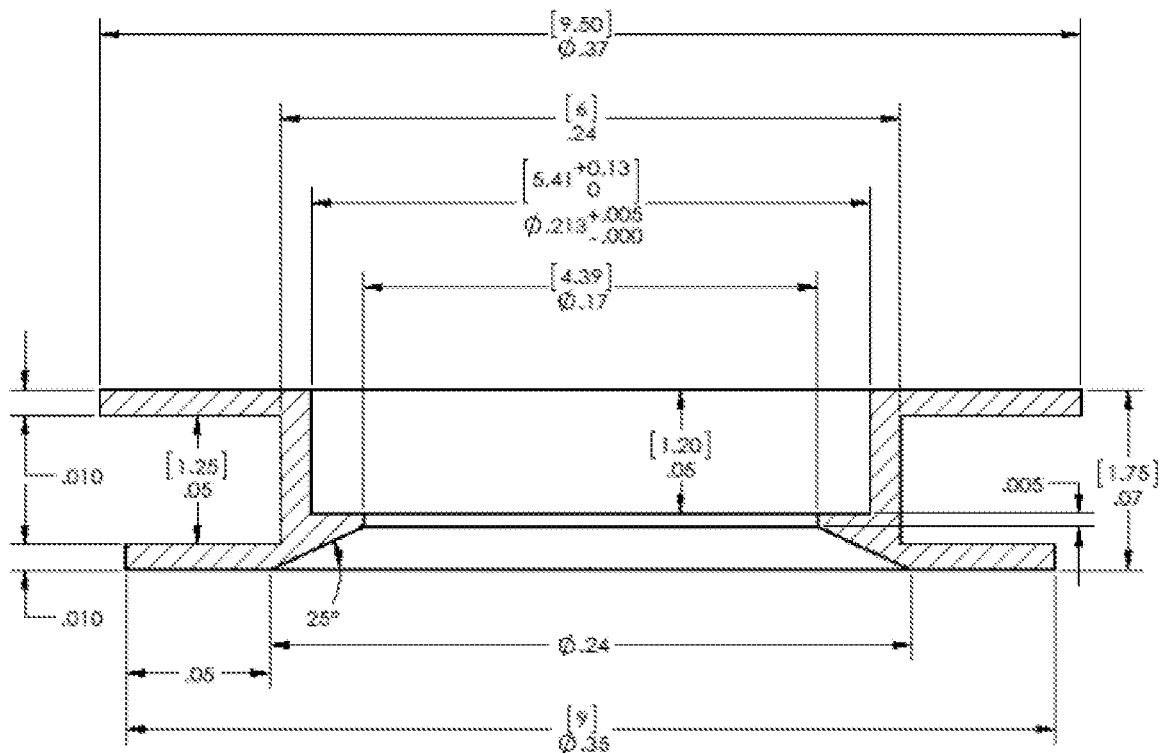
FIG. 17. Further example of the window frame shown in FIG. 12A.

Relocalization Using Microcartography. Verification of the WHRIL's ability to return to the same vasculature day after day can be accomplished by the visual identification of structures that maintain their morphology between imaging sessions. Two examples are the dextran-labeled blood vasculature (FIGS. 13C, 16) and the second harmonic generation (SHG) signal generated by the network of collagen I fibers present in the lung. Of these two, the blood vasculature is arguably the best structure for this identification as it is rather insensitive to slight deviations in focus and can accommodate any tilt that might occur. The fine collagen I network, is more susceptible to these influences as well as the dependence of SHG signals upon the orientation of the laser polarization relative to the fibers. Still, these factors may be overcome by 1) taking care to consistently position the mouse on the microscope stage in the same orientation, 2) utilizing leveling screws that come on many xy stage plates, and 3) by acquiring z-stacks of images into the tissue, enabling definitive revisualization of even these fine structures. Components of the collagen network are immediately recognizable from day to day, despite some morphological changes (e.g. straightening of collagen fibers) between imaging sessions. This is so for z-projections with many slices (e.g., 8 slices) or just two slices. In either case, the determination of the luminal or abluminal positioning of tumor cells will not be affected by stage tilt as both the vasculature and tumor cells will be impacted identically and their relative positioning easily determined.

Image Processing/Analysis. Occasionally a small amount of lateral drift was observed in time lapse movies. In these cases application of the StackReg plugin (Thevanaz et al. 1998) for ImageJ restored motion artifact free images. Unless otherwise noted in the figure legends, all images presented are the raw data acquired from the microscope with minimal adjustment of brightness and contrast and with a 0.5 pixel median filter applied to reduce salt and pepper noise.

3D Reconstruction. The difference between the luminal and abluminal sides of the lung vasculature can be difficult to ascertaining from single, or just a few optical sections. Three dimensional reconstructions dramatically aids in this determination by providing the full endothelial surface allowing the visualization of exactly when and where the tumor cells cross the endothelium. For three-dimensional reconstructions, TIFF image data was imported into Imaris 8.4 (BitPlane). To more clearly distinguish between structures inside and outside of vasculature, the blue and green signal was removed from the topmost z slice. Background subtraction was performed followed by salt and pepper noise removal using a median filter with a 3×3×1 kernel. After import of images into Imaris, isosurfaces were created based upon manually-selected intensity threshold values chosen to best match the overlap of the generated surface with the raw data. After surface generation, small objects (30 μm³ for blood vessels, 20 μm³ for tumor and macrophages) were removed. The reconstructed surfaces were overlaid on the raw image to ensure the surfaces fit the raw data in all 3 axes. This reconstruction could be performed equally well for either the blood averaged, or the raw data.

Results

Figures 12A, 12B, 12C, 12D, 12E, 12F:
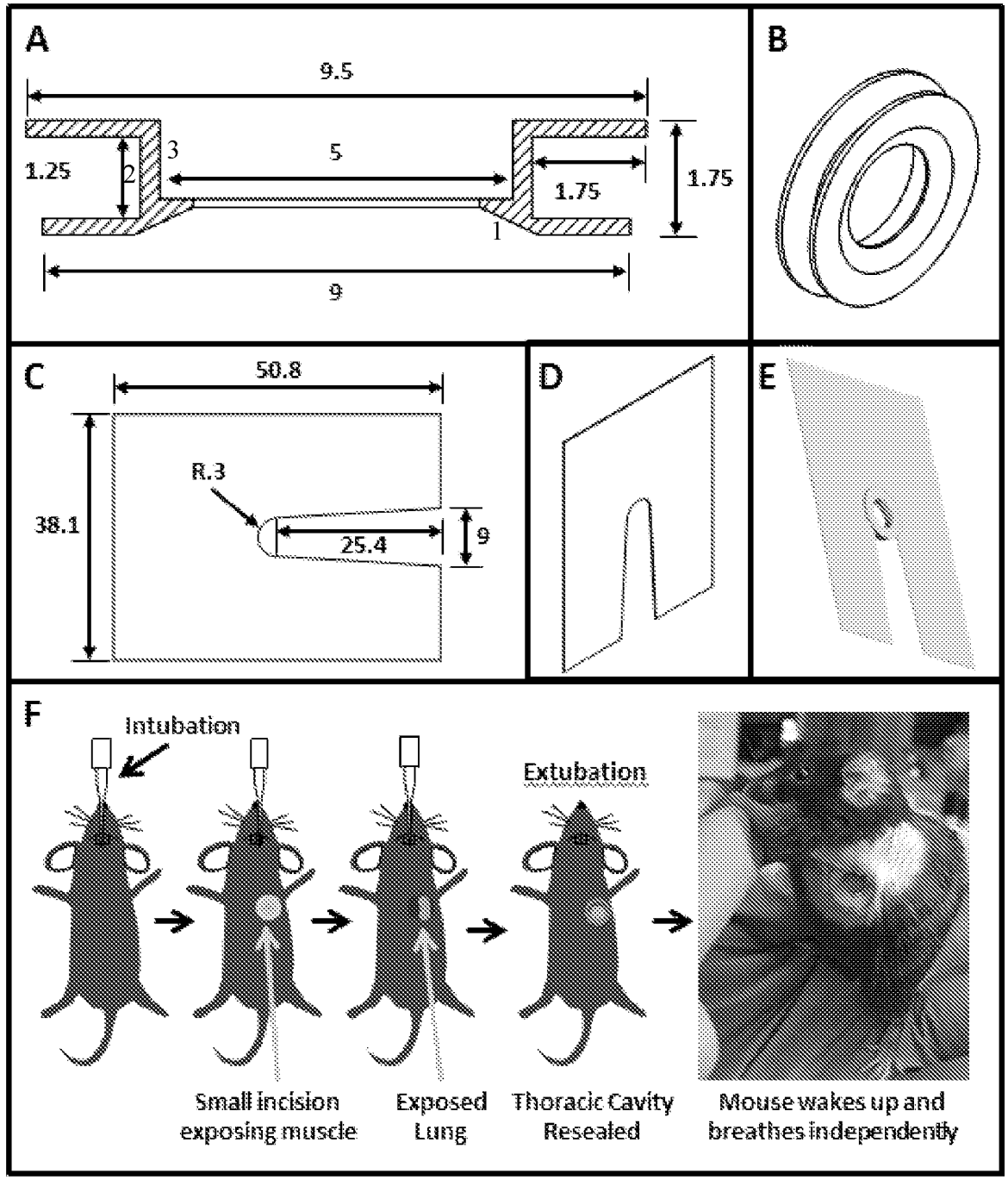
FIG. 12A-12F. Design of WHRIL and Overview of Surgical Protocol. A) Computer aided design of the window frame. The beveled edge on the lower part of the frame rests against the tissue, such as lung tissue. The sides of the frame provide a groove into which the ribcage and/or tissue flap fits. The frame provides a recess for a window, e.g. a coverslip. The overall thickness of the frame is less than the working distance of the objective lens of the microscope. All dimensions are listed in millimeters. B) 3 dimensional perspective view of the window frame showing the beveled, tissue-facing side. C) Computer aided design of the window fixturing plate consisting of a thin plate with a recess that accepts and fixtures the window frame shown in A) and B). The thickness of the fixturing plate is chosen so that the plate will slip between the upper lip of the window frame and skin/ribcage positioned in the groove of the window frame. All dimensions are listed in millimeters. The fixturing plate is made of 0.008 in stainless steel shim stock. D) 3 dimensional perspective view of the window fixuring plate. E) 3 dimensional rendering of the window inserted into the fixturing plate. F) Overview of the surgical protocol. Mouse is first intubated using a 22 gauge catheter, connected to a ventilator and a small incision is made through the skin, muscle and ribs. Finally, the window is affixed in place with a combination of sutures and adhesive which reseals the thoracic cavity allowing the mouse to be extubated, wake up, and breathe independently.

WHRIL Design. The design of the implantable WHRIL is shown in FIGS. 12A&B. This window is composed of a stainless steel frame with a central aperture that accepts a 5 mm coverslip. A 1.75 mm groove around the circumference allows the window to be inserted snugly between the ribs. A bevel on the thoracic side conforms to the curvature of the lung, and its overall thickness is chosen to be less than the working distance of the objective lens (2 mm).

Fixturing Plate Design. As described in the surgery section below, the lung tissue itself is isolated from motion caused by breathing and the heartbeat. However, because the WHRIL is part of the ribcage, the window and frame are susceptible to motion of the entire thorax created by the mouse's inspiration. Minimization of this movement is essential to acquiring high resolution images as motion artifacts of even a few microns can blur and distort images. Part of this immobilization is accomplished by securing the window to the stage via a thin fixturing plate (FIGS. 12C&D) that is slid between the window's outer edge and the mouse's skin. FIG. 12E demonstrates how the window is captured by the fixturing plate. Use of an inverted microscope enables the window to be affixed to the xy stage while allowing the thorax and lung tissue to expand and contract naturally without any impediment to respiration. This keeps the imaged tissue completely immobilized relative to the microscope objective, allows the use of relatively slow image acquisition speeds (~1 fps), and obviates the need for gated acquisition or post processing.

Minimally Invasive Surgery. To create a permanent, implantable, optical imaging window that would allow the mouse to breathe independently while imaging, a protocol was developed as summarized in FIG. 12F and described in detail in the methods section. Briefly, before surgery, mice are anesthetized and the hair over the left thorax is depilated. Intubation and mechanical ventilation allows the mouse to survive during the brief time the seal of the thoracic cavity is broken. Skin and muscle over the chest wall is excised and ribs 6 & 7 are partially removed. The window is inserted into the gap in the chest wall and secured with a combination of sutures and adhesive, resealing the thoracic cavity and allowing the mouse to breathe independently after extubation. Mice over three months of age are best suited for surgery as the trachea and ribs are thicker and more durable. If performed correctly, the window will become an integral part of the chest wall and the thoracic cavity will be well sealed with the lung tissue fully adhered to the coverglass. This allows the mouse to live comfortably and be imaged daily up to the protocol allowance (two weeks).

Physiological impact of the WHRIL. To determine the effect of the surgery and long-term use of the WHRIL on the physiology of the mouse, a series of experiments was performed, looking at reactivity to handling, appearance, behavior, weight, and white and red blood cell count (te Velde et al. 2003), which were previously used to validate an abdominal imaging window (Ritsma et al. 2012). Overall, only mild alterations in behavior such as ruffled fur (in 1 out of 8 mice) and a slightly elevated white blood cell count (in 1 other of the 8 mice) were observed. Across the cohort, there was a slight drop, and partial recovery, in weight and red blood cell count, which was less than a standard deviation.

To test whether the WHRIL induces any tissue damage (e.g., necrotic zones or abnormal lung architecture), hematoxylin and eosin stained sections of lung tissue were analyzed from under the window and away from the window at several different time points. Independent evaluation by two pathologists identified no regions of necrosis and mild ventilator induced alveolar distention regardless of association with the window. Focal collections of proteinaceous fluid and occasional reactive pneumocytes were noted in some of the alveoli at POD 3. These changes were not apparent on POD 7 or 14.

Image quality and comparison to vacuum window. Just as with a previously published vacuum window (Entenberg et al. 2015), the WHRIL allows the continuous acquisition of stable, high-resolution, time-lapse images of the lung vasculature over multiple time scales extending from minutes to hours. As an example, the WHRIL has been used to capture images of single cells in the healthy lung. The high spatial stability of the imaged field allows the application of a previously published blood averaging technique (Entenberg et al. 2015), which eliminates the transient disruption of vascular signal that occurs when unlabeled erythrocytes and leukocytes pass through the lumen of the vessels and occlude the fluorescent dextran.

In order to determine the positioning of cells relative to the vasculature (luminal vs. abluminal), mice were utilized where the endothelial cells were transgenically labeled with fluorescently tagged VE-Cadherin (B6.FVB-Tg(Cdh5-cre) 7Mlia/J x B6.Cg-Gt(ROSA)26Sortm14(CAG-tdTomato) Hze). This gives a clear dividing line between the intra- and the extravascular space that persists even when the blood serum (and hence, the fluorescent dextran) is occluded by the presence of a cell in the lumen of the vessel.

Re-localization of regions of interest within the window. Unlike the previously published lung imaging windows, the WHRIL has the added benefit of offering multiple views into the lung vasculature over days and even weeks. Given that the surface of the lung is a fairly uniform meshwork of nearly identical capillaries and alveoli, relocalization of the same micro-vasculature day after day is extremely challenging. This is especially so when the mouse is removed from and returned to the microscope stage on consecutive imaging sessions since arbitrary rotations and translations of the tissue relative to the objective lens occur. This challenge was overcome using a technique called in vivo microcartography (Dunphy et al. 2009).

Figures 13A, 13B, 13C, 13D:
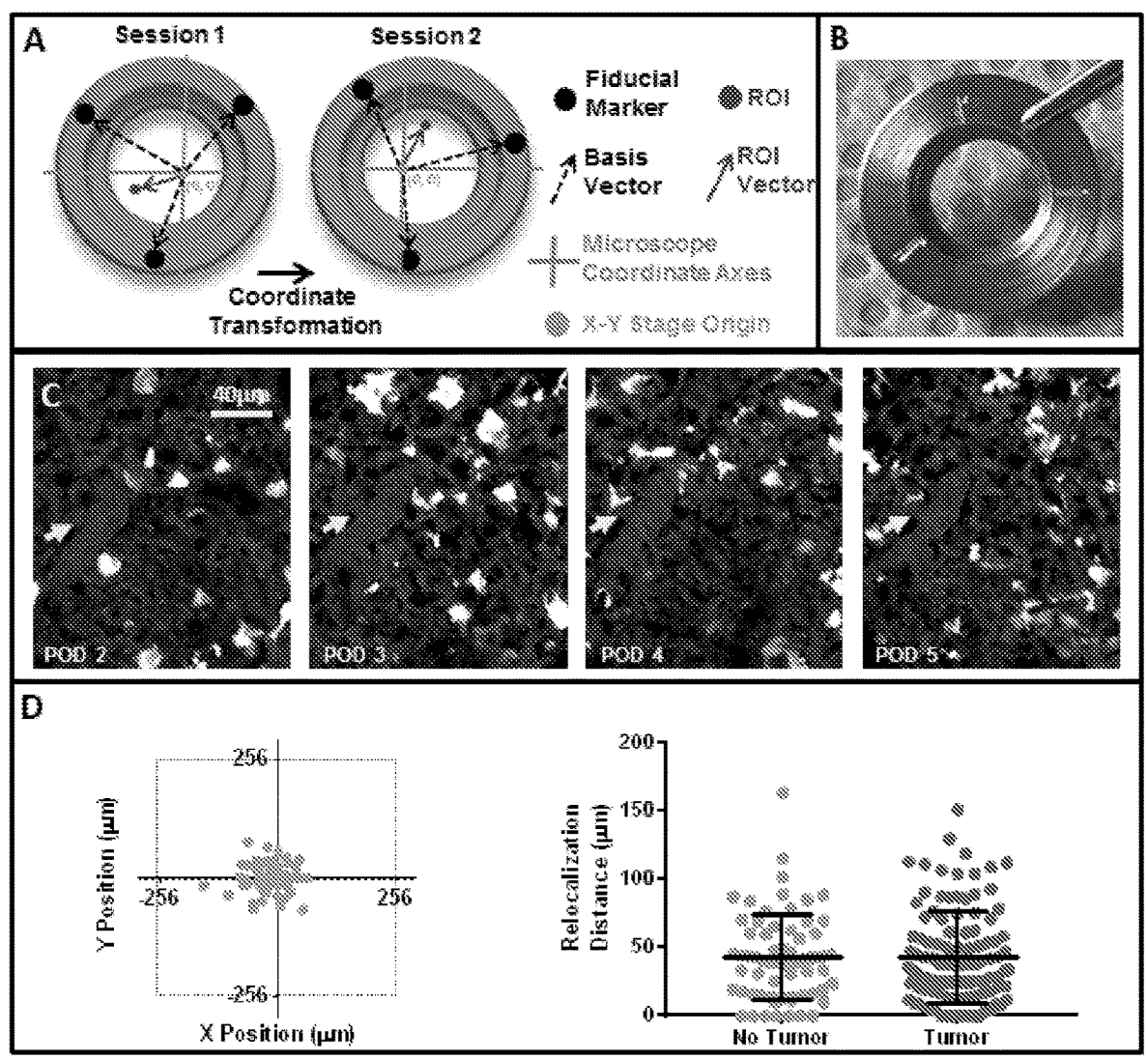
FIG. 13A-13D. Microcartography enables relocalization of positions within the window day after day. A) Easily identifiable fiducial marks etched on the window frame (black dots) serve as navigational reference points and, along with the xy stage origin (dots), form a set of basis vectors (black dashed arrows) from which a coordinate transformation connecting each imaging session may be derived. This transformation takes into account both rotation and translation of xy stage coordinate axes (lines) relative to the mouse from session to session. The derived transformation can then be used to predict the coordinates of any previously measured location. B) Picture of the window with etched fiducial marks. C) Multiphoton images of a single optical section in the lung showing the same microvasculature relocated using microcartography over 4 consecutive days. Arrows indicate the location of same exact microvessel branch point in each day. Optical resolution=250 nm. D) Reproducibility of Microcartography. Left: Scatter plot (n=65 fields of view) showing the ability of microcartography to relocalize a region of interest to within a single 512×512 µm field of view (box). Right: Graph showing the precision of microcartography's ability to relocate a region of interest in both healthy (n=65 fields of view, mean=42.7±31.4 µm s.e.m) and tumor bearing lung tissue (n=113 fields of view, mean=42.8±33.3 µm s.e.m).

In Dunphy et al. (2009), microspheres placed within a dorsal skin fold chamber acted as fiducial marks whose position could be easily located and recorded at the beginning of each imaging session. These marks were then used to create a set of basis vectors and construct a coordinate transformation that allowed re-localization of any point previously recorded. The scheme is diagrammatically demonstrated in (FIG. 13A) where basis vectors (black arrows) formed by the xy stage's origin (dot) and the fiducial marks (dots) can be defined on sequential imaging sessions (Session 1 and Session 2). In this current implementation, the microspheres are substituted with grooves etched onto the window frame prior to implantation (FIG. 13B). These grooves serve as the fiducial marks and remain fixed relative to the tissue within the window. Using this technique one can relocate the same exact microvasculature daily (FIG. 13C). The procedure works reliably and reproducibly, consistently relocating structures. The left hand plot of FIG. 13D demonstrates the x and y repositioning accuracy; 100% of the time, structures are relocated within a single 512×512 µm imaging field of view (box). These same data can be redrawn as a dot plot showing the overall precision of microcartography's ability to relocate a region of interest (right plot, dots). These data can then be directly compared to the relocalization ability in mice bearing lung metastases (right plot, dots).

Figures 14A, 14B, 14C:
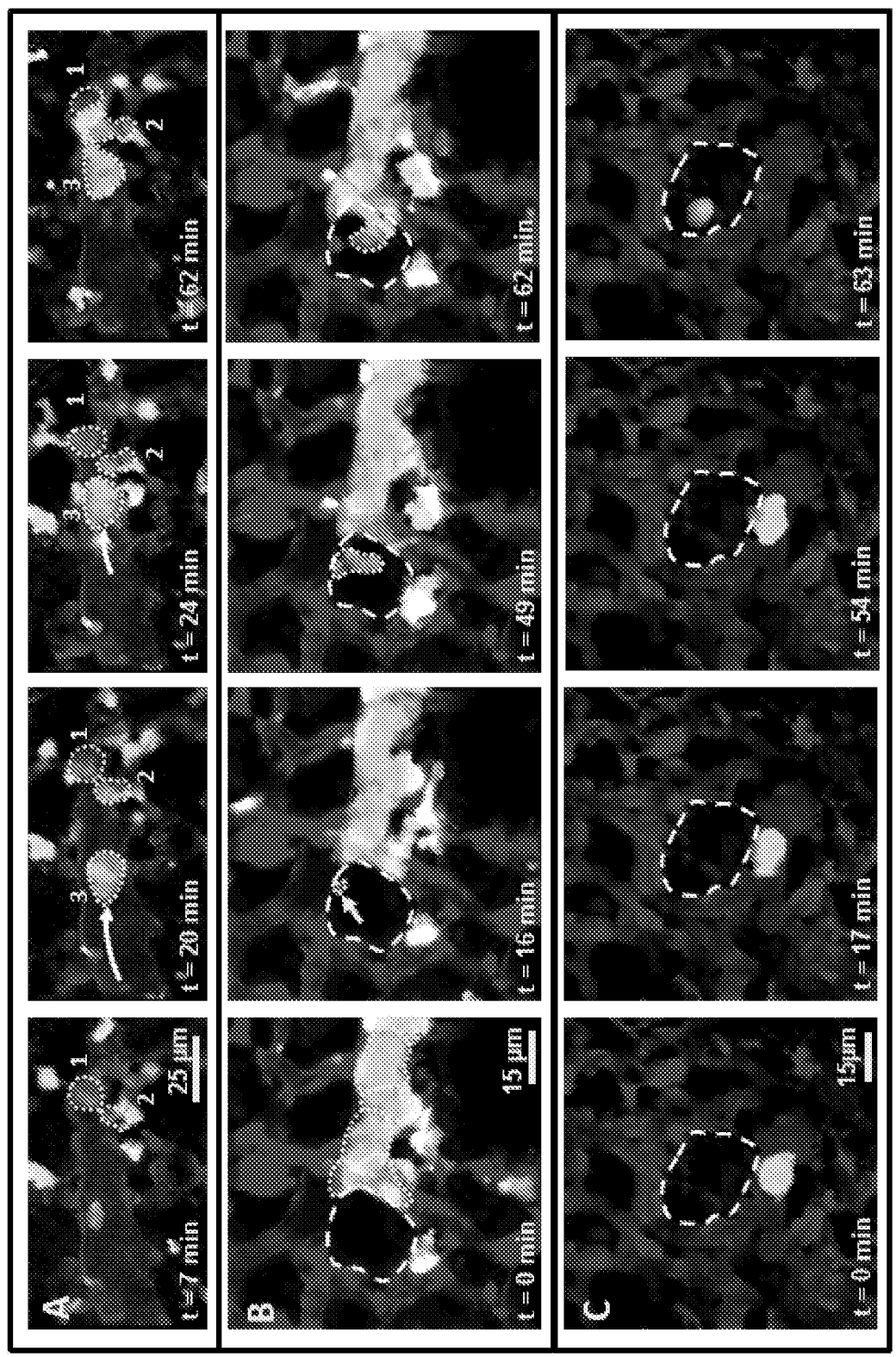
FIG. 14A-14C. The WHRIL allows visualization of tumor cell arrival (panel A) and extravasation in both experimental (panel B) and spontaneous (panel C) metastasis models. A) Stills from a time-lapse movie showing individual tumor cells (numbers 1, 2 & 3, dotted outlines) arriving in the lung vasculature after intravenous injection. The frame at t=7 min shows two tumor cells residing in the vasculature. At 20 min, a third tumor cell arrives. By 62 minutes, the three cells form a cluster in the vasculature. B) Stills from a time-lapse intravital imaging movie of experimentally metastasized (tail vein injected) tumor cells (dotted outlines) lodged in the vasculature ~60 minutes after tail vein injection. 16 minutes after the start of imaging, an invasive protrusion (arrow and small dotted outline) can be seen crossing the endothelium into the alveolus (large dashed white outline). Extravasation of the tumor cell has completed by t=62 minutes. Images are a z projection of 3 optical sections taken 3 µm apart and processed with the blood averaging algorithm so as to better determine the boundaries of the vasculature. C) Stills from a time-lapse intravital imaging movie of a spontaneously metastasizing tumor cell in the vasculature 1 day after window implantation. The cell crosses the endothelium into the alveolar space (dashed white outline) by t=63 min. Images are a z projection of 2 optical sections taken 3 µm apart and processed with the blood averaging algorithm so as to better determine the boundaries of the vasculature. All panels: Optical resolution=250 nm.
Figure 15:
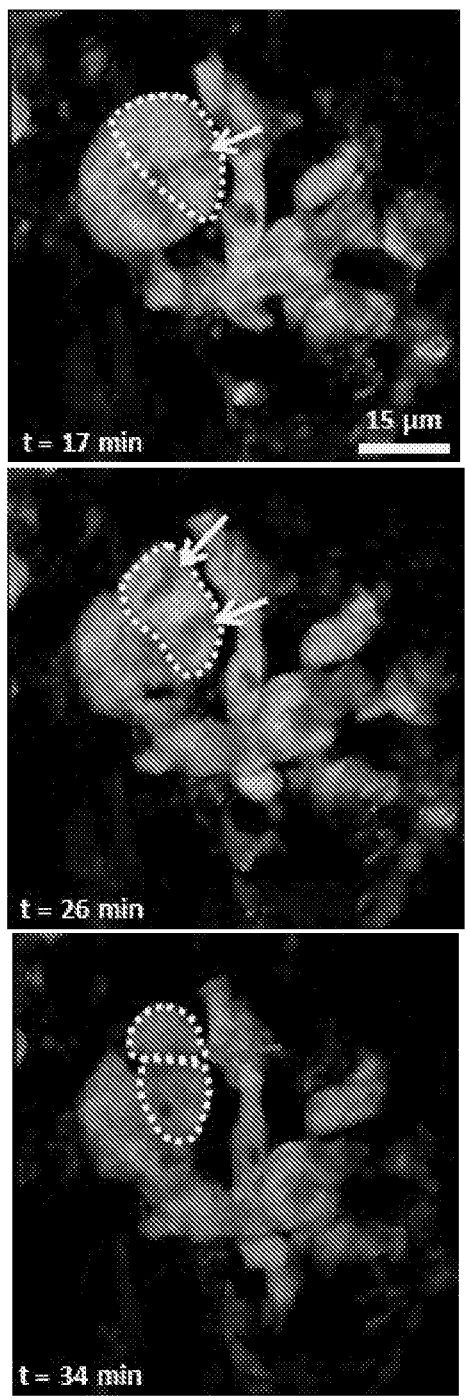
FIG. 15. The WHRIL allows visualization of subcellular structures and tumor cell growth over several days. Visualization of apparent tumor cell division in a spontaneous metastasis model: Stills from a time-lapse movie showing a cluster of tumor cells 2 days after arrival into the lung vasculature and 8 days after implantation of the WHRIL. In one cell (dashed line in t=17 min and t=26 min) subcellular organelles can be seen undergoing movement characteristic of chromosomal alignment (arrow at t=17 min) and separation (arrows at t=26 min) followed by cytokinesis (dashed lines and arrow at t=34 min). Optical resolution=250 nm.

Imaging of metastatic cancer cells in the lung. In order to demonstrate the utility of the WHRIL, multiple stages of metastatic progression of breast cancer in the lung were imaged in both experimental as well as spontaneous metastasis models. Using the WHRIL, high-resolution, real time images of single cells were captured as they arrive to the vascular bed of the lung (FIG. 14A) and cross the endothelium (FIGS. 14B&C). The high resolution of this technique is sufficient to capture motion of subcellular organelles. For instance, FIG. 15 shows unlabeled organelles, potentially condensed DNA, moving in a pattern characteristic of chromosomal separation during cell division.

Further, the growth of a small number of disseminated tumor cells into micrometastases was imaged. This was accomplished using the commonly employed experimental metastasis model where tumor cells are directly injected into the vasculature as well as in a model where the tumor cells disseminate spontaneously from an orthotopically growing primary tumor. These observations of tumor cell arrival, endothelial crossing, and growth into micrometastases represent the first reported instances in the literature.

Given that the WHRIL enables the return to the same vasculature day after day, one can determine the fate of tumor cells without having to continuously image them. For example, when a disseminating tumor cell first arrives to the lung, one can identify it by visualizing and recording its position. Thus, even when one is unable to record events that occur during a relatively brief time interval (such as tumor cell transendothelial migration or disappearance through apoptosis or recirculation), one can still determine the cell's fate by using microcartography to return to the same exact field of view on subsequent imaging sessions. Co-registration of the two images clearly shows disappearance of the cell (FIG. 16A) or its transendothelial migration (FIG. 16B) which can be verified by the juxtaposition of the tumor cell relative to the vasculature.

Finally, the dynamics of the interaction between tumor cells, macrophages and endothelial cells have been investigated within micrometastases. In the primary tumor, the juxtaposition of these three cell types form the microanatomical structure known as tumor microenvironment of metastasis (TMEM), which has been shown to be the sole mechanism for hematogenous dissemination. In the primary tumor, TMEM function is visualized and identified by the transient leakage of vascular contents into the interstitum (Harney et al. 2015).

Looking in formalin fixed, paraffin embedded tissues from patients, TMEM structures were also found in breast cancer metastases in the lung. This led to stipulation that one would be able to observe TMEM function in the live lung with intravital imaging. Using the WHRIL, time-lapse imaged TMEM structures were obtained in lung metastases, as well as, for the first time, TMEM associated transient vascular leakage in the lung. To discern this leakage from other systemic changes in blood flow, the extravascular dextran located adjacent to the TMEM was quantified and directly compared to the vascular signal at three other distant locations within the imaged field of view. Not only does the temporal profile of the TMEM associated signal drastically differ from the vascular measurements, it also does not display the random fluctuations observed within the vasculature that are due to passing unlabeled erythrocytes and leukocytes, as mentioned in the section on blood averaging above. These data, along with the steady vascular morphology observed over time, eliminate the possibility that the TMEM associated extravascular dextran signal is due to systemic blood flow changes or a change in optical focus.

Discussion

An implantable, permanent window has been developed and validated for repeated visualization of the murine lung with high-resolution multiphoton or confocal microscopy over weeks. This window, and its accompanying minimally invasive surgical protocol, reproduce the capability of existing murine lung imaging windows (Entenberg et al. 2015) to produce stable, high-resolution images of the lung vasculature over an extended single imaging session. However, unlike any other murine lung imaging window, the WHRIL dramatically reduces the invasiveness of the surgery and reseals the thoracic cavity. This makes it possible for the mouse to recover from anesthesia, breathe independently (both between and during imaging sessions), and live with this "transparent ribcage" for weeks. Immobilization of the lung tissue, accomplished with a thin (<10 μm) layer of adhesive, obviates the need for high-speed gated imaging (Vinegoni et al. 2014) or other specialized ventilation or image processing techniques (Fiole et al. 2016, Presson et al. 2011). This results in a simplified experimental setup during imaging and makes the WHRIL accessible for use in a wide range of applications using a multiphoton microscope.

The recent publication of the vacuum imaging window (Entenberg et al. 2015) discussed the long and rich history of intravital imaging in the lung extending back to Wearn and German's first observations in cats (Wearn et al. 1926). Since that time, numerous techniques have been developed in a variety of species. However, only two groups have been successful in developing permanent implantable windows. In 1963 De Alva and Ranier developed a 2 in diameter window for use in dogs and rabbits, and in 1994 Fingar and Wieman developed a 1 in diameter window for use in rats.

While both of these windows allowed survival of the animal after surgery, neither was capable of stabilizing the lung tissue for high resolution imaging, and both were limited to use in large animals. Only the work of Kimura and Hoffman (2010) was able to attain a view of the murine lung over multiple days, though only at low resolution. This was accomplished, however, by a protocol that involved multiple surgeries, cutting open the chest wall, as well as surgically exposing the trachea (to verify correct intubation) for each imaging session. The lung tissue was additionally immobilized using sustained PEEP during imaging. This protocol is extremely invasive, prevents healing of the chest wall, potentially causes damage to the alveoli from overexpansion of the lung tissue and runs a high risk of infection.

These techniques fall in line with the conclusions presented in Fiole and Tournier's 2016 review of the field in which they observe that "strategies developed in order to overcome movements of the thorax caused by breathing and heartbeats remain the chief drawback of the technique and a major source of invasiveness". This led them to the conclusion that, "In broad terms, greater invasiveness leads to better resolution." The WHRIL addresses these concerns, is the first permanent window to be developed for small animals such as mice, and provides a solution that is both high-resolution, and minimally invasive.

Using the WHRIL provides the first direct visualization, with single cell resolution, of all of the steps of metastasis, including arrival, extravasation, growth, and progression to micro-metastases. This was done using both the experimental, and importantly, the more clinically relevant spontaneously-metastasizing cancer models. Furthermore, the activity of the tripartite structure called Tumor MicroEnvironment of Metastasis (TMEM) was observed in metastatic lung lesions suggesting that the same mechanism of hematogenous dissemination seen in the primary tumor is present and functional in metastatic lesions.

The major limitation of this technology, as with optical imaging techniques of all tissues, is its relatively limited depth of penetration. This limitation means that pathologies that occur in the larger bronchioles and vessels deep within the lung are inaccessible for high resolution optical imaging. Despite this limitation, the technique is clinically relevant, particularly to the field of cancer since "lung metastases are to be found at the periphery of the lung", as is large cell carcinoma and a portion of squamous cell carcinoma metastasis (Braman and Whitcomb 1975, Herold et al. 1996, Scholten et al. 1977, Travis et al. 2011). Further, this technology provides a significant advantage over standard ex vivo assays (Bernal et al. 2008, Miyao et al. 2006), which disconnect the tissue from the physiological gas and cell exchange, as well as the newly developed in vivo imaging methods, which are limited in duration and do not extend beyond 12 hours (Entenberg et al. 2015, Rodriguez-Tirado et al. 2016). While these assays have produced advances in pulmonary research, they only provide a snapshot view of dynamic processes.

The ability to view the same lung tissue with subcellular resolution over multiple days has the potential to address many unanswered questions in lung pathology. As one example (of many), the role and importance of circulating tumor cell clusters in metastasis has recently garnered renewed interest. Originally published as part of a series of investigations into the functional dependence of experimental metastasis (intravenous injection of tumor cells) on tumor cell number, size, and viability, Fidler (1973) reported that clusters of tumor cells injected directly into the vasculature resulted in an increased number of metastases when compared with an equivalent injection of single cells. These results were recapitulated in experiments by Liotta et al. (1976), and most recently, Aceto et al. (2014).

All of these studies, however, have relied upon the intravenous injection of tumor cells and endpoint evaluations of gross metastases in the lung with all steps in between remaining hidden. In addition to being rather aphysiological (tumor cells do not metastasize clinically as a huge bolus of cells injected into the vasculature) interpretation of these data relies upon the assumption that the metastases that develop weeks after injection are directly derived from the injected clusters. While possible, there is no direct evidence for this assumption. What would be required to address this question directly is the ability to repeatedly visualize the lungs of these mice with single-cell resolution and follow the sites where tumor cells arrive and seed over the period of weeks it takes them to grow into macro-metastases. This would enable the determination of the sequence of biological events and cause and effect relationships between them.

Only the WHRIL provides the ability to directly visualize tumor cell arrival and ultimate fate during spontaneous metastatic progression over weeks, enabling investigations not before possible into the mechanisms underlying tumor cell seeding, survival, dormancy, and growth.

REFERENCES

Aceto, N. et al. Circulating tumor cell clusters are oligoclonal precursors of breast cancer metastasis. Cell 158, 1110-1122, doi:10.1016/j.cell.2014.07.013 (2014).

Bernal, P. J. et al. Nitric-oxide-mediated zinc release contributes to hypoxic regulation of pulmonary vascular tone. Circ Res 102, 1575-1583, doi:10.1161/CIRCRESAHA.108.171264 (2008).

Braman, S. S. & Whitcomb, M. E. Endobronchial metastasis. Arch Intern Med 135, 543-547 (1975).

Cahalan M. D., I. Parker, S. H. Wei, M. J. Miller, Real-time imaging of lymphocytes in vivo, Curr Opin Immunol 15(4) (2003) 372-7.

Clunie D. A., D. K. Dennison, D. Cram, K. R. Persons, M. D. Bronkalla, H. R. Primo, Technical Challenges of Enterprise Imaging: HIMSS-SIIM Collaborative White Paper, J Digit Imaging 29(5) (2016) 583-614.

Dasari S., P. Weber, C. Makhloufi, E. Lopez, C. L. Forestier, Intravital Microscopy Imaging of the Liver following Leishmania Infection: An Assessment of Hepatic Hemodynamics, J Vis Exp (101) (2015) e52303.

De Alva, W. E. & Rainer, W. G. A method of high speed in vivo pulmonary microcinematography under physiologic conditions. Angiology 14, 160-164 (1963).

Deroulers C., D. Ameisen, M. Badoual, C. Gerin, A. Granier, M. Lartaud, Analyzing huge pathology images with open source software, Diagn Pathol 8 (2013) 92.

De Zanet S., T. Rudolph, R. Richa, C. Tappeiner, R. Sznitman, Retinal slit lamp video mosaicking, Int J Comput Assist Radiol Surg 11(6) (2016) 1035-41.

Dorand R. D., D. S. Barkauskas, T. A. Evans, A. Petrosiute, A. Y. Huang, Comparison of intravital thinned skull and cranial window approaches to study CNS immunobiology in the mouse cortex, Intravital 3(2) (2014).

Duda, D. G. et al. Malignant cells facilitate lung metastasis by bringing their own soil. Proc Natl Acad Sci USA 107, 21677-21682, doi:10.1073/pnas.1016234107 (2010).

Dunn K. W., T. A. Sutton, R. M. Sandoval, Live-animal imaging of renal function by multiphoton microscopy, Curr Protoc Cytom Chapter 12 (2007) Unit129.

Dunphy, M. P., Entenberg, D., Toledo-Crow, R. & Larson, S. M. In vivo microcartography and subcellular imaging of tumor angiogenesis: a novel platform for translational angiogenesis research. Microvasc Res 78, 51-56, doi:10.1016/j.mvr.2009.03.008 (2009).

DuPage, M., Dooley, A. L. & Jacks, T. Conditional mouse lung cancer models using adenoviral or lentiviral delivery of Cre recombinase. Nat Protoc 4, 1064-1072, doi:10.1038/nprot.2009.95 (2009).

Entenberg D., I. Aranda, Y. Li, R. Toledo-Crow, D. Schaer, Y. Li, Multimodal microscopy of immune cells and melanoma for longitudinal studies., Proc of SPIE 6081 (2006) 62-73.

Entenberg D., D. Kedrin, J. Wyckoff, E. Sahai, J. Condeelis, J. E. Segall, Imaging tumor cell movement in vivo, Curr Protoc Cell Biol 2013, p. Unit197.

Entenberg D., C. Rodriguez-Tirado, Y. Kato, T. Kitamura, J. W. Pollard, J. Condeelis, In vivo subcellular resolution optical imaging in the lung reveals early metastatic proliferation and motility, Intravital 4(3) (2015) 1-11.

Entenberg D., Roorda R D, Toledo-Crow R, Non-linear microscope for imaging of the neural systems in live drosophila, OSA BioMed 2004.

Entenberg D., J. Wyckoff, B. Gligorijevic, E. T. Roussos, V. V. Verkhusha, J. W. Pollard, J. Condeelis, Setup and use of a two-laser multiphoton microscope for multichannel intravital fluorescence imaging, Nat Protoc 6(10) (2011) 1500-20.

Fidler, I. J. The relationship of embolic homogeneity, number, size and viability to the incidence of experimental metastasis. Eur J Cancer 9, 223-227 (1973).

Fingar, V. H., Taber, S. W. & Wieman, T. J. A new model for the study of pulmonary microcirculation: determination of pulmonary edema in rats. J Surg Res 57, 385-393, doi:10.1006/jsre.1994.1159 (1994).

Fiole, D. & Tournier, J. N. Intravital microscopy of the lung: minimizing invasiveness. J Biophotonics 9, 868-878, doi: 10.1002/jbio.201500246 (2016).

Friedl P., J. Locker, E. Sahai, J. E. Segall, Classifying collective cancer cell invasion, Nat Cell Biol 14(8) (2012) 777-83.

Gligorijevic B., A. Bergman, J. Condeelis, Multiparametric classification links tumor microenvironments with tumor cell phenotype, PLoS Biol 12(11) (2014) e1001995.

Harney A. S., E. N. Arwert, D. Entenberg, Y. Wang, P. Guo, B. Z. Qian, M. H. Oktay, J. W. Pollard, J. G. Jones, J. S. Condeelis, Real-Time Imaging Reveals Local, Transient Vascular Permeability, and Tumor Cell Intravasation Stimulated by TIE2hi Macrophage-Derived VEGFA, Cancer Discov 5(9) (2015) 932-43.

Harney A. S., Y. Wang, J. S. Condeelis, D. Entenberg, Extended Time-lapse Intravital Imaging of Real-time Multicellular Dynamics in the Tumor Microenvironment, J Vis Exp (112) (2016) e54042.

Harper K. L., M. S. Sosa, D. Entenberg, H. Hosseini, J. F. Cheung, R. Nobre, A. Avivar-Valderas, C. Nagi, N. Girnius, R. J. Davis, E. F. Farias, J. Condeelis, C. A. Klein, J. A. Aguirre-Ghiso, Mechanism of early dissemination and metastasis in Her2+ mammary cancer, Nature 540 (2016) 589-612.

Heindl A., S. Nawaz, Y. Yuan, Mapping spatial heterogeneity in the tumor microenvironment: a new era for digital pathology, Lab Invest 95(4) (2015) 377-84.

Herold, C. J., Bankier, A. A. & Fleischmann, D. Lung metastases. Eur Radiol 6, 596-606 (1996).

Karagiannis G. S., J. M. Pastoriza, Y. Wang, A. S. Harney, D. Entenberg, J. Pignatelli, V. P. Sharma, E. A. Xue, E. Cheng, T. M. D'Alfonso, J. G. Jones, J. Anampa, T. E. Rohan, J. A. Sparano, J. S. Condeelis, M. H. Oktay, Neoadjuvant chemotherapy induces breast cancer metastasis through a TMEM-mediated mechanism, Science translational medicine 9(397) (2017).

Kedrin D., B. Gligorijevic, J. Wyckoff, V. V. Verkhusha, J. Condeelis, J. E. Segall, J. van Rheenen, Intravital imaging of metastatic behavior through a mammary imaging window, Nat Methods 5(12) (2008) 1019-21.

Kimura, H. et al. Real-time imaging of single cancer-cell dynamics of lung metastasis. J Cell Biochem 109, 58-64, doi:10.1002/jcb.22379 (2010).

Kothari S., J. H. Phan, T. H. Stokes, M. D. Wang, Pathology imaging informatics for quantitative analysis of whole-slide images, Journal of the American Medical Informatics Association 20(6) (2013) 1099-1108.

Kwasnitschka T., K. Koser, J. Sticklus, M. Rothenbeck, T. Weiss, E. Wenzlaff, T. Schoening, L. Triebe, A. Steinfuhrer, C. Devey, J. Greinert, DeepSurveyCam—A Deep Ocean Optical Mapping System, Sensors (Basel) 16(2) (2016) 164.

Legesse F. B., O. Chernayskaia, S. Heuke, T. Bocklitz, T. Meyer, J. Popp, R. Heintzmann, Seamless stitching of tile scan microscope images, J Microsc 258(3) (2015) 223-32.

Liotta, L. A., Saidel, M. G. & Kleinerman, J. The significance of hematogenous tumor cell clumps in the metastatic process. Cancer Res 36, 889-894 (1976).

Liou H. L., J. T. Myers, D. S. Barkauskas, A. Y. Huang, Intravital imaging of the mouse popliteal lymph node, J Vis Exp (60) (2012).

Lloyd M. C., K. A. Rejniak, J. S. Brown, R. A. Gatenby, E. S. Minor, M. M. Bui, Pathology to enhance precision medicine in oncology: lessons from landscape ecology, Adv Anat Pathol 22(4) (2015) 267-72.

Loo B. W., Jr., W. Meyer-Ilse, S. S. Rothman, Automatic image acquisition, calibration and montage assembly for biological X-ray microscopy, J Microsc 197 (Pt 2) (2000) 185-201.

Looney M. R., E. E. Thornton, D. Sen, W. J. Lamm, R. W. Glenny, M. F. Krummel, Stabilized imaging of immune surveillance in the mouse lung, Nat Methods 8(1) (2011) 91-6.

Masedunskas A., N. Porat-Shliom, M. Tora, O. Milberg, R. Weigert, Intravital microscopy for imaging subcellular structures in live mice expressing fluorescent proteins, J Vis Exp (79) (2013).

Miyao, N. et al. Various adhesion molecules impair microvascular leukocyte kinetics in ventilator-induced lung injury. Am J Physiol Lung Cell Mol Physiol 290, L1059-1068, doi:10.1152/ajplung.00365.2005 (2006).

Ovchinnikov D. A., W. J. van Zuylen, C. E. DeBats, K. A. Alexander, S. Kellie, D. A. Hume, Expression of Gal4-dependent transgenes in cells of the mononuclear phagocyte system labeled with enhanced cyan fluorescent protein using Csflr-Gal4VP16/UAS-ECFP double-transgenic mice, J Leukoc Biol 83(2) (2008) 430-3.

Presson, R. G., Jr. et al. Two-photon imaging within the murine thorax without respiratory and cardiac motion artifact. Am J Pathol 179, 75-82, doi10.1016/j.ajpath.2011.03.048 (2011).

Price D. L., S. K. Chow, N. A. Maclean, H. Hakozaki, S. Peltier, M. E. Martone, M. H. Ellisman, High-resolution large-scale mosaic imaging using multiphoton microscopy to characterize transgenic mouse models of human neurological disorders, Neuroinformatics 4(1) (2006) 65-80.

Ritsma L., E. J. Steller, E. Beerling, C. J. Loomans, A. Zomer, C. Gerlach, N. Vrisekoop, D. Seinstra, L. van Gurp, R. Schafer, D. A. Raats, A. de Graaff, T. N. Schumacher, E. J. de Koning, I. H. Rinkes, O. Kranenburg, J. van Rheenen, Intravital microscopy through an abdominal imaging window reveals a pre-micrometastasis stage during liver metastasis, Science translational medicine 4(158) (2012) 158ra145.

Rodriguez-Tirado C., T. Kitamura, Y. Kato, J. W. Pollard, J. S. Condeelis, D. Entenberg, Long-term High-Resolution Intravital Microscopy in the Lung with a Vacuum Stabilized Imaging Window, J Vis Exp (116) (2016).

Scholten, E. T. & Kreel, L. Distribution of lung metastases in the axial plane. A combined radiological-pathological study. Radiol Clin (Basel) 46, 248-265 (1977).

Sellers S. L., G. W. Payne, Intravital microscopy of the inguinal lymph node, J Vis Exp (50) (2011).

Seshamani S., W. Lau, G. Hager, Real-time endoscopic mosaicking, Med Image Comput Comput Assist Interv 9 (Pt 1) (2006) 355-63.

te Velde, E. A. et al. Impaired healing of cutaneous wounds and colonic anastomoses in mice lacking thrombin-activatable fibrinolysis inhibitor. J Thromb Haemost 1, 2087-2096 (2003).

Thevenaz, P., Ruttimann, U. E. & Unser, M. A pyramid approach to subpixel registration based on intensity. IEEE Trans Image Process 7, 27-41, doi:10.1109/83.650848 (1998).

Travis, W. D. Classification of lung cancer. Semin Roentgenol 46, 178-186, doi:10.1053/j.ro.2011.02.003 (2011).

Vinegoni C., S. Lee, R. Gorbatov, R. Weissleder, Motion compensation using a suctioning stabilizer for intravital microscopy, Intravital 1(2) (2012) 115-121.

Vinegoni, C., Lee, S., Feruglio, P. F. & Weissleder, R. Advanced Motion Compensation Methods for Intravital Optical Microscopy. IEEE J Sel Top Quantum Electron 20, doi:10.1109/JSTQE.2013.2279314 (2014).

Walter T., D. W. Shattuck, R. Baldock, M. E. Bastin, A. E. Carpenter, S. Duce, J. Ellenberg, A. Fraser, N. Hamilton, S. Pieper, M. A. Ragan, J. E. Schneider, P. Tomancak, J. K. Heriche, Visualization of image data from cells to organisms, Nat Methods 7(3 Suppl) (2010) S26-41.

Wearn, J. T., Barr, J. S. & German, W. J. The Behavior of the Arterioles and Capillaries of the Lung. Experimental Biology and Medicine 24, 114-115, doi:10.3181/00379727-24-3250 (1926).

Weigert R., N. Porat-Shliom, P. Amornphimoltham, Imaging cell biology in live animals: ready for prime time, J Cell Biol 201(7) (2013) 969-79.

Wyckoff J., B. Gligorijevic, D. Entenberg, J. Segall, J. Condeelis, High-Resolution multiphoton imaging of tumors in vivo., Live Cell Imaging: A Laboratory Manual, Cold Spring Harbor Laboratory Press 2010, pp. 441-461.

Wyckoff J., B. Gligorijevic, D. Entenberg, J. Segall, J. Condeelis, High-resolution multiphoton imaging of tumors in vivo, Cold Spring Harbor Protocols 2011(10) (2011) 1167-84.

Zinselmeyer B. H., J. N. Lynch, X. Zhang, T. Aoshi, M. J. Miller, Video-rate two-photon imaging of mouse footpad—a promising model for studying leukocyte recruitment dynamics during inflammation, Inflamm Res 57(3) (2008) 93-6.

What is claimed is:

1. A method of high-resolution intravital imaging of lung tissue in a subject using a microscope, comprising:
   a) exposing the lung tissue in the subject by anesthetizing the subject and making a circular incision through the skin and adjacent ribs of the subject, lateral to the sternum and superior to the last floating rib;
   b) attaching a window frame to the subject so that the lung tissue is viewable through the window; wherein the window frame is attached by securing the window frame in the circular incision so that the adjacent ribs are positioned in a groove of the window frame; wherein the window frame comprises fiducial marks; and wherein the window frame is adhered to the lung tissue by raising the window frame away from the lung tissue, dispensing a quick-setting adhesive on the underside of the window frame, and expanding the lung to make contact with the window frame until the adhesive sets, suturing tissue around the window frame to provide a complete surgical closure, and sealing the thoracic cavity by applying an adhesive to a cover glass and adhering it to the expanded lung tissue and the inner recess of the window frame;
   c) following recovery of the subject from surgery, attaching the window frame to a microscope stage with a window fixturing plate that is movable relative to the optical axis of the microscope in at least x- and y-directions, wherein the window frame is attached to the microscope stage and stabilized for imaging by placing a fixturing plate, comprising portions defining a slotted recess sized to accommodate the window frame, between skin of the subject and an outside lip of the window frame, and placing the subject on the stage of the microscope; and
   d) acquiring through the window high-magnification, high-resolution overlapping images of the lung tissue in a mosaic pattern and stitching the images together to produce a low-magnification, high-resolution overview image of the lung tissue that preserves subcellular resolution, thereby obtaining high-resolution intravital images of the lung tissue in a subject.

2. The method of claim 1, wherein the fixturing plate comprises portions defining a circular hole for the window and a circular recess that holds the window frame.

3. The method of claim 1, wherein the fixturing plate comprises portions defining a slotted recess that holds the window frame.

4. The method of claim 1, wherein the fixturing plate is made of metal and/or plastic.

5. The method of claim 1, wherein the window frame is attached to the subject using adhesive.

6. The method of claim 1, comprising attaching the window frame to the lung tissue and applying saline within the window frame before the window is affixed to the window frame to cover the lung tissue with saline.

7. The method of claim 1, wherein additional stabilization of the lung tissue is provided by affixing a rigid backing to a side of the lung tissue opposite to the objective lens of the microscope.

8. The method of claim 7, wherein the rigid backing is made of one or more of rubber, plastic and metal.

9. The method of claim 1, wherein the window frame is made of metal and/or plastic.

10. The method of claim 1, wherein the fixturing plate is placed between the skin of the subject and the outside lip of the window frame to stabilize the lung tissue, wherein the fixturing plate has a recess for holding the window frame, and wherein the fixturing plate is secured to the microscope stage.

11. The method of claim 1, wherein the window frame comprises a plurality of fiducial markers.

12. The method of claim 1, wherein fiducial markers on the window frame serve as navigational reference points and, along with the xy stage origination, form a set of vectors from which a coordinate transformation connecting repeated imaging sessions can be derived.

13. The method of claim 1, wherein the window frame comprises
   a beveled edge that rests against the lung tissue,
   a groove into which a skin flap or ribcage fits, and
   a recess for the window.

14. The method of claim 1, wherein images are obtained using a low-magnification, high-numerical aperture, long-working distance objective lens.

15. The method of claim 14, wherein the lens is 25×1.05NA.

16. The method of claim 1, wherein the lung tissue is imaged to a depth of at least 100 μm with a step size of 5 μm between each z-slice.

17. The method of claim 1, wherein in step d), the images are obtained in a specific order so that the spatial relationships of the images is maintained and the overall architecture of the lung tissue is reconstructed.

18. The method of claim 1, wherein cells or other structures in the lung tissue of interest are labeled using genetically encoded fluorescent proteins or injectable fluorescent dyes.

19. The method of claim 1, wherein the window frame and window are chronically implanted in the subject.

20. The method of claim 1, wherein the method is used to visualize tumor cell movement, extravasation, tumor growth, tumor cell progression to metastases, or dynamics of interactions among cells including tumor cells, macrophages and endothelial cells, and subcellular dynamics including cell division, invasive protrusion and signaling secretion.

21. The method of claim 1, wherein the microscope is a multiphoton or confocal microscope.

22. The method of claim 1, wherein images obtained by the method do not require further processing to remove motion artifacts.

23. The method of claim 1, wherein the subject is a mammal.

24. The method of claim 1, wherein the subject is a mouse, rat, gerbil or rabbit.

25. The method of claim 1, wherein the subject is a laboratory animal.

26. The method of claim 1, wherein the window frame is made of stainless steel that has undergone passivation prior to implantation of the window frame in the subject.

27. The method of claim 1, wherein the window frame is secured using a suture that has been threaded between the adjacent ribs before the window frame is positioned in the incision.

28. The method of claim 1, wherein the quick-setting adhesive is cyanoacrylate.

29. The method of claim 1, wherein the fiducial marks on the window frame serve as navigational reference points and, along with the xy stage origination, form a set of vectors from which a coordinate transformation connecting repeated imaging sessions can be derived.

\* \* \* \* \*